US006143721A

United States Patent [19]
Janssen et al.

[11] Patent Number: 6,143,721
[45] Date of Patent: Nov. 7, 2000

[54] DOLASTATIN 15 DERIVATIVES

[75] Inventors: Bernd Janssen, Marlborough; Teresa Barlozzari, Wellesley; Andreas Haupt, Northborough, all of Mass.; Thomas Zierke, Bohl-Iggelheim; Andreas Kling, Mannheim, both of Germany

[73] Assignee: BASF Aktiengesellschaft, Rheinland-Pfalz, Germany

[21] Appl. No.: 08/896,394

[22] Filed: Jul. 18, 1997

[51] Int. Cl.$^7$ .................................................. A61K 38/00
[52] U.S. Cl. ................... 514/16; 514/2; 514/17; 530/328; 530/329; 530/330
[58] Field of Search .................. 530/329, 330, 530/328; 514/2, 16, 17

[56] References Cited

U.S. PATENT DOCUMENTS

| | | | |
|---|---|---|---|
| 4,816,444 | 3/1989 | Pettit et al. | 514/17 |
| 5,502,032 | 3/1996 | Haupt et al. | 514/17 |
| 5,504,191 | 4/1996 | Pettit et al. | 530/330 |
| 5,530,097 | 6/1996 | Pettit et al. | 530/330 |
| 5,554,725 | 9/1996 | Pettit | 530/330 |
| 5,807,984 | 9/1998 | Kling et al. | 530/330 |
| 5,831,002 | 11/1998 | Haupt et al. | 530/329 |

FOREIGN PATENT DOCUMENTS

| | | |
|---|---|---|
| 0 398 558 | 11/1990 | European Pat. Off. |
| 0 598 129 | 5/1994 | European Pat. Off. |
| 9323424 | 11/1993 | WIPO . |
| 96/18408 | 6/1996 | WIPO . |
| WO 96/40751 | 12/1996 | WIPO . |
| WO 96/40752 | 12/1996 | WIPO . |
| WO 97/17364 | 5/1997 | WIPO . |
| WO 97/22621 | 6/1997 | WIPO . |

OTHER PUBLICATIONS

Pettit, G.R., et al., "The Isolation and Structure of a Remarkable Marine Animal Antineoplastic Constituent: Dolastatin 10," *J. Am. Chem. Soc.* 109:6883–6885 (1987).

Bai, R., et al., "Structure–Activity Studies with Chiral Isomers and With Segments of the Antimitotic Marine Peptide Dolastatin 10," *Biochemical Pharmacology* 40(8):1859–1864 (1990).

Pettit, G.R., et al., "Antineoplastic Agents. 220. Synthesis of Natural (−)–Dolastatin 15," *J. Am. Chem. Soc.*, 113:6692–6693 (1991).

Bai, R., et al., "Dolastatin 15, a potent antimitotic depsipeptide derived from *Dolabella auricularia*. Interaction with tubulin and effects on cellular microtubules," *1–Pharmacology* Abstract 117: 10373g p. 41 (1992).

Pettit, G.R., et al., "Isolation and Structure of the Cytostatic Depsipeptide Dolastatin 13 from the Sea Hare *Dolabella auricularia*," *J. Am. Chem. Soc.*, 111(13):5015–5017 (1989).

Pettit, G.R., et al., "Antineoplastic Agents 337. Synthesis of Dolastatin–10 Structural Modifications," *Anti–Cancer Drug Design*, 10:529–544 (1995).

Miyazaki, K., et al., "Synthesis and Antitumor Activity of Novel Dolastatin–10 Analogs," *Chem. Pharm. Bull.*, 43(10):1706–1718 (1995).

Pettit, G.R., et al.,"Isolation and Structure of the Cytostatic Linear Depsipeptide Dolastatin 15," *J. Org. Chem.*, 54:6005–6006 (1989).

Pettit, G.R., et al., "The Dolastatins 20. A Convenient Synthetic Route to Dolastatin 15," *Tetrahedron*, 50(42):12097–12108 (1994).

Pettit, G.R., et al., Isolation of Dolastatins 10–15 from the Marine Mollusc *Dolabella Auricularia*, *Tetrahedron*, 49(42):9151–9170 (1993).

*Primary Examiner*—Marianne M. Cintins
*Assistant Examiner*—C. Delacroix-Muirheid
*Attorney, Agent, or Firm*—Hamilton, Brook, Smith & Reynolds, P.C.

[57] ABSTRACT

Compounds of the present invention include cell growth inhibitors which are peptides of Formula I, $$A\text{-}B\text{-}D\text{-}E\text{-}F\text{-}(G)_r\text{-}(K)_s\text{-}L \qquad (I),$$

and acid salts thereof, wherein A, B, D, E, F, G and K are α-amino acid residues, and s and r are each, independently, 0 or 1. L is a monovalent radical, such as, for example, an amino group, an N-substituted amino group, a β-hydroxylamino group, a hydrazido group, an alkoxy group, a thioalkoxy group, an aminoxy group, or an oximato group. The present invention also includes a method for treating cancer in a mammal, such as a human, comprising administering to the mammal an effective amount of a compound of Formula I in a pharmaceutically acceptable composition.

39 Claims, No Drawings

DOLASTATIN 15 DERIVATIVES

BACKGROUND OF THE INVENTION

A number of short peptides with significant activity as inhibitors of cell growth have been isolated from the Indian Ocean sea hare *Dolabella auricularia* (Bai et al., *Biochem. Pharmacology*, 40: 1859–1864 (1990); Beckwith et al., *J. Natl. Cancer Inst.*, 85: 483–488 (1993) and references cited therein). These include Dolastatins 1–10 (U.S. Pat. No. 4,816,444, issued to Pettit et al.) and Dolastatin-15 (European Patent Application No. 398558). Dolastatin 15, for example, markedly inhibits the growth of the National Cancer Institute's P388 lymphocytic leukemia (PS system) cell line, a strong predictor of efficacy against various types of human malignancies.

The exceedingly small amounts of the various Dolastatin peptides present in *Dolabella auricularia* (about difficulties in purifying amounts sufficient for evaluation and use, have motivated efforts toward the synthesis of these compounds (Roux et al., *Tetrahedron* 50: 5345–5360 (1994); Shioiri et al., *Tetrahedron* 49: 1913–24 (1993); Patino et al., *Tetrahedron* 48: 4115–4122 (1992) and references cited therein). Synthetic Dolastatin 15, however, suffers from drawbacks which include poor solubility in aqueous systems and the need for expensive starting materials for its synthesis. These, in turn, have led to the synthesis and evaluation of structurally modified Dolastatin 15 derivatives [cf.: *Biorg. Med. Chem. Lett.* 4: 1947–50 (1994); WO 93 03054; JP-A-06234790; WO 93 23424].

However, there is a need for synthetic compounds with the biological activity of Dolastatin 15 which have useful aqueous solubility and can be produced efficiently and economically.

SUMMARY OF THE INVENTION

Compounds of the present invention include cell growth inhibitors which are peptides of Formula I, $$A\text{-}B\text{-}D\text{-}E\text{-}F\text{-}(G)_r\text{-}(K)_s\text{-}L \qquad (I),$$

and acid salts thereof, wherein A, B, D, E, F, G and K are α-amino acid residues, and s and r are each, independently, 0 or 1. L is a monovalent radical, such as, for example, an amino group, an N-substituted amino group, a β-hydroxylamino group, a hydrazido group, an alkoxy group, a thioalkoxy group, an aminoxy group, or an oximato group.

Another aspect of the present invention includes pharmaceutical compositions comprising a compound of Formula I and a pharmaceutically acceptable carrier.

An additional embodiment of the present invention is a method for treating cancer in a mammal, such as a human, comprising administering to the mammal an effective amount of a compound of Formula I in a pharmaceutically acceptable composition.

DETAILED DESCRIPTION OF THE INVENTION

The present invention relates to peptides having antineoplastic activity. It also includes pharmaceutical compositions comprising these compounds and methods for treating cancer in a mammal, including a human, by administration of these compositions to the mammal.

Dolastatin 15, a peptide isolated from the sea hare *Dolabella auricularia*, is a potent inhibitor of cell growth. This compound, however, is present in trace quantities in the sea hare, and is thus difficult to isolate. Dolastatin 15 is also expensive to synthesize and suffers from poor aqueous solubility. As shown herein, however, Dolastatin 15 can serve as a starting point for the development of compounds which overcome these disadvantages while retaining antineoplastic activity or exhibiting greater antineoplastic activity than the natural product. Applicants have discovered that certain structural modifications of Dolastatin 15 provide compounds with a surprisingly improved therapeutic potential for the treatment of neoplastic diseases as compared to Dolastatin 10 and Dolastatin 15. Furthermore, the compounds of the present invention can be conveniently synthesized, as described below in detail.

For the purposes of the present invention, the term "monovalent radical" is intended to mean an electrically neutral molecular fragment capable of forming one covalent bond with a second neutral molecular fragment. Monovalent radicals include the hydrogen atom, alkyl groups, such as methyl, ethyl and propyl groups, halogen atoms, such as fluorine, chlorine and bromine atoms, aryl groups, such as phenyl and naphthyl groups, and alkoxy groups, such as methoxy and ethoxy groups. Two monovalent radicals on adjacent sigma-bonded atoms can also together form a pi bond between the adjacent atoms. Two monovalent radicals may also be linked together, for example, by a polymethylene unit, to form a cyclic structure. For example, the unit —N(R)R', wherein R and R' are each a monovalent radical, can, together with the nitrogen atom, form a heterocyclic ring. In addition, two monovalent radicals bonded to the same atom can together form a divalent radical, such as an oxygen atom or an alkylidene group, for example, a propylidene group.

For the purposes of the present invention, the term "normal alkyl" refers to an unbranched, or straight chain, alkyl group, for example, normal propyl (n-propyl, —$CH_2CH_2CH_3$).

The compounds of the present invention can be represented by Formula I, $$A\text{-}B\text{-}D\text{-}E\text{-}F\text{-}(G)_r\text{-}(K)_s\text{-}L \qquad (I),$$

wherein A, B, D, E, F, G, and K are α-amino acid residues; s and r are each, independently, 0 or 1; and L is a monovalent radical such as an amino group, an N-substituted amino group, a β-hydroxylamino group, a hydrazido group, an alkoxy group, a thioalkoxy group, an aminoxy group, or an oximato group.

The peptides of Formula I are generally composed of L-amino acids but they can contain one or more D-amino acids. In the following discussion, reference to a particular amino acid includes both enantiomers unless a specific enantiomer is indicated. The present compounds can also be present as salts with physiologically-compatible acids, including hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

The following is a description of the present invention, including a detailed description of individual components and of methods of using the claimed compounds.

Compounds of the Present Invention
Identity of A

In one embodiment, A is a proline derivative of Formula $II_a$,

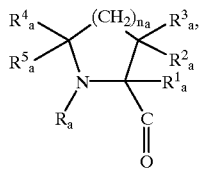

(II$_a$)

where $n_a$ is an integer, preferably 0, 1, 2, or 3. $R_a$ is a monovalent radical, such as a hydrogen atom or an unsubstituted or fluorine-substituted alkyl group, for example a normal, branched or cyclic $C_1$–$C_3$-alkyl group which is, optionally, substituted by from 1 to about 3 fluorine atoms; suitable examples include methyl, ethyl, isopropyl, 2-fluoroethyl, 2,2,2-trifluoroethyl, 1-methyl-2-fluoroethyl, 1-fluoromethyl-2-fluoroethyl or cyclopropyl; methyl, ethyl or isopropyl are preferred;

In this embodiment, $R^1_a$ is a monovalent radical, such as a hydrogen atom, an alkyl group, such as a methyl, ethyl or propyl group, or a phenyl group. The phenyl group can be substituted; suitable substituents include one or more halogen atoms, with fluorine, chlorine and bromine atoms preferred, $C_1$–$C_4$-alkyl groups, methoxy, ethoxy, trifluoromethyl or nitro groups. $R_a$ and $R^1_a$ together can also form a propylene bridge.

$R^2_a$/$R^3_a$/$R^4_a$ and $R^5_a$ are each, independently, a monovalent radical, such as a hydrogen atom or an alkyl, preferably, methyl, group.

In another embodiment, A is a substituted glycine derivative of Formula $III_a$,

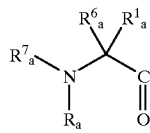

(III$_a$)

where $R_a$ has the meaning stated for $R_a$ in Formula $II_a$ and, $R^1_a$ is a monovalent radical, for example, a hydrogen atom or a $C_1$–$C_6$-alkyl group, preferably a methyl, ethyl or propyl group.

In this embodiment, $R^6_a$ is a monovalent radical, such as an alkyl, substituted alkyl, alkenyl, phenyl or substituted phenyl group. Suitable examples include methoxymethyl, 1-methoxyethyl, 1,1-dimethyl-hydroxymethyl, 1-trifluoromethylethyl, 1-trifluoromethyl-2,2,2-trifluoroethyl, vinyl, and 1-methylvinyl. Phenyl substituents can include one or more halogen atoms, preferably fluorine, chlorine or bromine atoms, and alkyl, methoxy, ethoxy, trifluoromethyl, and nitro groups.

When $R^1_a$ is an alkyl group, $R^6_a$ can also be a $C_1$–$C_6$-alkyl, cycloalkyl, unsubstituted benzyl or substituted benzyl group. Suitable benzyl substituents include one or more halogen atoms, such as fluorine, chlorine or bromine atoms, $C_1$–$C_4$-alkyl groups, and methoxy, ethoxy, trifluoromethyl and nitro groups.

$R^7_a$ is a monovalent radical, preferably a methyl, ethyl or isopropyl group.

In another embodiment, A is an α-amino acid derivative of Formula $IV_a$,

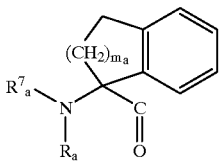

(IV$_a$)

where $m_a$ is an integer, preferably 1 or 2, and $R_a$ and $R^7_a$ have the meanings stated for these substituents in Formula $III_a$.

In another embodiment, A is an α-amino acid derivative of Formula $V_a$,

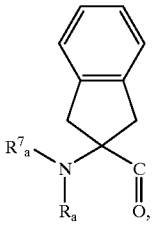

(V$_a$)

where $R_a$ and $R^7_a$ have the meanings stated for $R_a$ and $R^7_a$ in Formula $III_a$.

In a further embodiment, A is a substituted proline derivative of Formula $VI_a$,

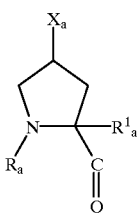

(VI$_a$)

where $R_a$ and $R^1_a$ have the meanings stated for $R_a$ and $R^1_a$ in Formula $II_a$, and $X_a$ is a monovalent radical, preferably a hydroxyl, alkoxy, for example, methoxy or ethoxy, group or a fluorine atom.

In another embodiment, A is a thiaprolyl derivative of Formula $VII_a$,

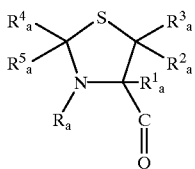

(VII$_a$)

where $R_a$, $R^1_a$, $R^2_a$, $R^3_a$, $R^4_a$ and $R^5_a$ have the meanings stated for the respective substituents in Formula $II_a$.

In another embodiment, A is a 1,3-dihydroisoindole derivative of Formula $VIII_a$

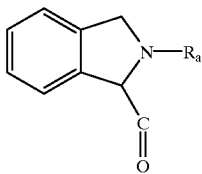

(VIII$_a$)

where R$_a$ has the meaning stated for R$_a$ for Formula II$_a$.

In another embodiment, A is a 2-azabicyclo[2.2.1]heptane-3-carboxylic acid derivative of Formula IX$_a$,

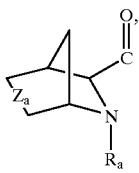

(IX$_a$)

where Z$_a$ is a single or double bond and R$_a$ has the meaning stated for Formula II$_a$. The 3-carbonyl substituent can have either the exo or endo orientation.

In another embodiment, A is an α-amino acid derivative of Formula X$_a$,

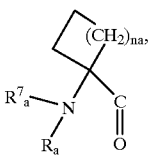

(X$_a$)

where n$_a$ has the meaning as stated for n$_a$ for Formula II$_a$, and R$^7_a$ and R$_a$ have the meanings as stated for R$^7_a$ and R$_a$ for Formula III$_a$.

Identity of B

B is a valyl, isoleucyl, allo-isoleucyl, norvalyl, 2-tert-butylglycyl or 2-ethylglycyl residue. B can also be an α-amino acid residue of Formula II$_b$,

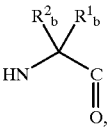

(II$_b$)

in which R$^1_b$ and R$^2_b$ are each a monovalent radical. R$^1_b$ is, preferably, a hydrogen atom and R$^2_b$ is, for example, an alkyl, alkoxyalkyl or alkenyl group. In preferred embodiments, R$^2_b$ is a cyclopropyl group, a normal or branched butyl, preferably tertiary-butyl, group, a methoxymethyl group, a 1-methoxyethyl group or a 1-methylvinyl group. Additionally, R$^1_b$ and R$^2_b$ together can be an isopropylidene group.

Identity of D

D is an N-alkylvalyl, N-alkyl-2-ethylglycyl, N-alkyl-2-tert-butylglycyl, N-alkyl-norleucyl, N-alkyl-isoleucyl, N-alkyl-allo-isoleucyl or N-alkyl-norvalyl residue, where the N-alkyl group is preferably a methyl group or an ethyl group.

In another embodiment, D is an α-amino acid residue of Formula II$_d$,

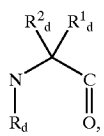

(II$_d$)

where R$_d$ has the meaning stated for R$_a$ in Formula III$_a$, R$^1_d$ is a monovalent radical, preferably a hydrogen atom, and R$^2_d$ is a monovalent radical, for example, an alkyl, alkoxyalkyl or alkenyl group. In preferred embodiments, R$^2_d$ is a cyclopropyl group, a normal or branched butyl, preferably tertiary-butyl, group, a methoxymethyl group, a 1-methoxyethyl group or a 1-methylvinyl group. such as a cyclopropyl group, a methoxymethyl group, a 1-methoxyethyl group or a 1-methylvinyl group. Additionally, R$^1_d$ and R$^2_d$ together can form an isopropylidene group.

Alternatively, D can be a proline derivative of Formula III$_d$,

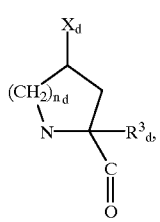

(III$_d$)

where n$_d$ is an integer, for example, 1 or 2, and R$^3_d$ has the meaning stated for R$^1_a$ in Formula III$_a$. X$_d$ is a monovalent radical, preferably a hydrogen atom, and, in the case where n$_d$ equals 1, can also be a hydroxy or alkoxy, for example, methoxy or ethoxy, group or a fluorine atom.

Identity of E

E is a prolyl, thiazolidinyl-4-carbonyl, homoprolyl or hydroxyprolyl residue, or a cyclic α-amino carboxylic acid residue of Formula II$_e$,

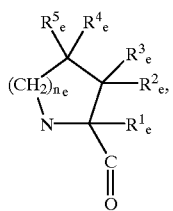

(II$_e$)

where n$_e$ is an integer, preferably 0, 1 or 2. R$^1_e$ has the meaning stated for R$^1_a$ in Formula III$_a$. R$^2_e$ and R$^3_e$ are each a monovalent radical, and can be, independently, a hydrogen atom or an alkyl, preferably methyl, group. R$^4_e$ is a monovalent radical, preferably a hydrogen atom, a hydroxy, alkoxy, for example, methoxy or ethoxy, group or a fluorine atom. R$^5_e$ is a monovalent radical, preferably a hydrogen atom or a fluorine atom. In the case where n$_e$ is 1, R$^3_e$ and R$^4_e$ can together form a double bond, or R$^4_e$ and R$^5_e$ can together be a double-bonded oxygen radical. In the case where n$_e$ has the value 1 or 2, R$^1_e$ and R$^2_e$ can together form a double bond.

In another embodiment, E is a 2- or 3-aminocyclopentanecarboxylic acid residue of Formula III$_e$,

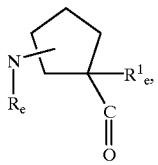
(III$_e$)

where R$_e$ is an alkyl group, such as methyl or ethyl, and R$^1_e$ has the meaning stated for R$^1_a$ in Formula III$_a$.

Identity of F

F is a prolyl, thiazolidinyl-4-carbonyl, homoprolyl or hydroxyprolyl residue. F can also be a cyclic α-amino acid residue of Formula II$_f$,

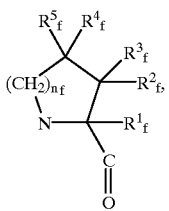
(II$_f$)

where n$_f$ is an integer, preferably 0, 1 or 2. R$^1_f$ has the meaning stated for R$^1_a$ in Formula III$_a$. R$^2_f$ and R$^3_f$ are each a monovalent radical, and can be, independently, a hydrogen atom or an alkyl, preferably methyl, group. R$^4_f$ is a monovalent radical, preferably a hydrogen atom, a hydroxy, alkoxy, for example, methoxy or ethoxy, group or a fluorine atom. R$^5_f$ is a monovalent radical, preferably a hydrogen atom or a fluorine atom. In the case where n$_f$ has the value 1, R$^3_f$ and R$^4_f$ together can form a double bond or R$^4_f$ and R$^5_f$ can together be a double-bonded oxygen radical.

In the case where n$_f$ has the value 1 or 2, R$^1_f$ and R$^2_f$ can together form a double bond.

In another embodiment, F is a 2- or 3-aminocyclopentanecarboxylic acid residue of Formula III$_f$

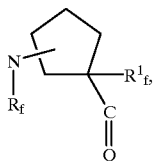
(III$_f$)

where R$_f$ is a monovalent radical, such as a methyl or ethyl group, and R$^1_f$ has the meaning stated for R$^1_a$ in Formula III$_a$.

In another embodiment, F is an N-alkylglycyl or N-alkylalanyl residue, and the alkyl group is, preferably, a methyl group or an ethyl group.

Identity of G

G is an α-amino acid residue of Formula II$_g$.

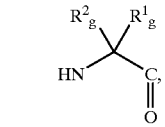
(II$_g$)

wherein R$^1_g$ is a hydrogen atom, or an alkyl group, for example, methyl, ethyl or n-propyl. R$^2_g$ can be, for example, a hydrogen atom, or an alkyl, arylalkyl, heteroarylalkyl or aryl group. Preferably, R$^2_g$ is an ethyl, isopropyl, tert-butyl, isobutyl, 2-methylpropyl, cyclohexylmethyl, benzyl, thiazolyl-2-methyl, pyridyl-2-methyl, n-butyl, 2,2-dimethylpropyl, naphthylmethyl, or n-propyl group, or a substituted or unsubstituted phenyl group. Suitable phenyl substituents include one or more halogen, preferably fluorine, chlorine or bromine, atoms, C$_1$–C$_4$-alkyl groups, methoxy, ethoxy, nitro or trifluoromethyl groups or a dioxomethylene group. Alternately, R$^1_g$ and R$^2_g$ can, together with the α-carbon atom, form a cyclopentane or cyclohexane ring or a benzo-fused cyclopentane ring, such as, for example, the indanyl group.

Identity of K

K is an α-amino acid residue of Formula II$_k$,

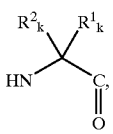
(II$_k$)

wherein R$^1_k$ has the identity stated for R$^1_g$ in Formula II$_g$, and R$^2_k$ has the identity stated for R$^2_g$ in Formula II$_g$.

Identity of L

In one embodiment, L is an amino or substituted amino group of Formula II$_l$,

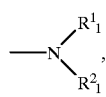
(II$_l$)

where R$^1_l$ is a monovalent radical, such as a hydrogen atom, a normal or branched, saturated or unsaturated C$_1$–C$_{18}$-alkoxy group, a substituted or unsubstituted aryloxy group, a substituted or unsubstituted aryl-C$_1$–C$_6$-alkoxy group, or a substituted or unsubstituted aryloxy-C$_1$–C$_6$-alkoxy or heteroaryl-C$_1$–C$_6$-alkoxy group. The aryl group is preferably a phenyl or naphthyl group. The heteroaryl group is a 5- or 6-membered, preferably nitrogen-, oxygen- or sulfur-containing, ring system, such as, for example, a heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine. Suitable aryl substituents include one or more halogen, preferably fluorine, bromine or chlorine, atoms, C$_1$–C$_4$-alkyl groups, methoxy, ethoxy or trifluoromethyl groups, a dioxymethylene group or nitro groups.

$R^2_l$ is a monovalent radical, such as a hydrogen atom, a normal or branched, saturated or unsaturated $C_1$–$C_{18}$-alkyl group, a $C_3$–$C_{10}$-cycloalkyl group, a substituted or unsubstituted aryl group, or a substituted or unsubstituted heteroaryl group. The aryl group is preferably a phenyl or naphthyl group. The heteroaryl group is a 5- or 6-membered, preferably nitrogen-, oxygen- or sulfur-containing, ring system, such as, for example, a heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine. Suitable aryl substituents include one or more halogen, preferably fluorine, bromine or chlorine, atoms, $C_1$–$C_4$-alkyl groups, methoxy, ethoxy or trifluoromethyl groups, a dioxymethylene group or nitro groups.

$R^2_l$ can, alternately, be of Formula $II_r$,

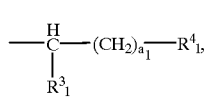

(II$_r$)

where $a_l$ is an integer, such as 0, 1, 2, 3, 4 or 5. $R^3_l$ is a monovalent radical, preferably a lower alkyl group, such as a methyl, ethyl, propyl or isopropyl group. $R^4_l$ is a monovalent radical, which can be a saturated or partially unsaturated carbocyclic system comprising from about 3 to about 10 carbon atoms, a substituted or unsubstituted aryl or heteroaryl group, with aryl and heteroaryl and preferred substituents having the meaning stated for $R^2_l$ in Formula $II_l$.

$R^2_l$ can also be a substituent of Formula $III_r$, $$-(CH_2)_2-W_l-R^5_l \quad (III_r),$$

wherein $W_l$ is an oxygen or sulfur atom or an $N-R^6_l$ group. $R^5_l$ is a monovalent radical, such as a hydrogen atom, a $C_1$–$C_4$-alkyl or $C_3$–$C_7$-cycloalkyl group or a substituted or unsubstituted aryl or arylmethyl group, with aryl and its preferred substituents having the meaning stated for $R^2_l$ from Formula $II_l$. $R^6_l$ is a monovalent radical, preferably a hydrogen atom, a $C_1$–$C_4$-alkyl group or a $C_3$–$C_7$-cycloalkyl group, a $C_1$–$C_{18}$-alkanoyl group, a benzoyl group or a substituted or unsubstituted aryl or arylmethyl group, with aryl and its preferred substituents having the meaning stated for $R^2_l$ in Formula $II_l$.

$R^2_l$ can, alternately, be a substituent of Formula $IV_r$, $$-(CH_2)_{b_l}-Z_l \quad (IV_r)$$

where $b_l$ is an integer, preferably 2, 3 or 4. $Z_l$ can be a monovalent radical such as a formyl, aminocarbonyl or hydrazinocarbonyl group, or a cyclic or acyclic acetal or thioacetal group.

$R^2_l$ can also be a substituent of Formula $V_r$,

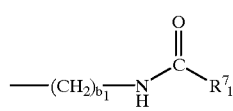

(V$_r$)

in which $b_l$ has the above-mentioned meaning. $R^7_l$ can be a monovalent radical, such as a polyglycol group of the formula $-O-(CH_2-CH_2-O)_{d'}-CH_3$, where d, is an integer, preferably in the range from about 2 to about 4 or from about 40 to about 90.

$R^2_l$ can further be a carbohydrate of Formula $VI_r$,

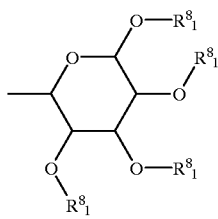

(VI$_r$)

where $R^8_l$ is a monovalent radical, such as a hydrogen atom, a $C_1$–$C_4$-alkanoyl or alkyl group, a benzoyl group or a benzyl group.

L can also be a β-hydroxylamino group of Formula $III_l$,

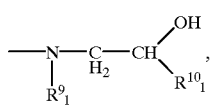

(III$_l$)

where $R^9_l$ is a monovalent radical such as a hydrogen atom, a $C_1$–$C_6$-alkyl group or a substituted or unsubstituted aryl group, with aryl and its preferred substituents having the meaning stated for $R_l$. $R^{10}_l$ is a monovalent radical, preferably a hydrogen atom, alkyl, for example, methyl, or a phenyl group.

When r and/or s is 1, L can also be an amino group of Formula $IV_l$,

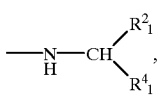

(IV$_l$)

where $R^2_l$ and $R^4_l$ are each a monovalent radical. $R^2_l$ and $R^4_l$ can also be linked by a carbon-carbon bond.

Another subclass of compounds of this invention includes peptides of Formula I wherein L is a hydrazido group of Formula $V_l$,

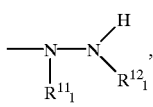

(V$_l$)

and $R^{11}_l$ is a monovalent radical, preferably a hydrogen atom. $R^{12}_l$ can be a monovalent radical such as a hydrogen atom, a normal or branched $C_1$–$C_8$-alkyl group, a $C_3$–$C_8$-cycloalkyl group, a $C_3$–$C_8$-cycloalkyl-$C_1$–$C_4$-alkyl group or a substituted or unsubstituted aryl, heteroaryl, aryl-$C_1$–$C_4$-alkyl or heteroaryl-$C_1$–$C_4$-alkyl group, where aryl, heteroaryl and their preferred substituents can be selected from among the options listed for $R^2_l$.

When r and/or s is 1, $R^{11}_l$ can also be selected from among the options listed above for $R^{12}_l$, and the two radicals together can additionally form a propylene or butylene bridge.

Another subclass of compounds of this invention includes peptides of Formula I wherein L is a monovalent radical of the formula —O—$R^{13}{}_I$, or the formula —S—$R^{13}{}_I$, where $R^{13}{}_I$ is a monovalent radical, such as a $C_3$–$C_{10}$-cycloalkyl group, a normal or branched $C_2$–$C_{16}$-alkenylmethyl group or a $C_1$–$C_{16}$-alkyl group which can be substituted by from 1 to about 5 halogen, preferably fluorine, atoms.

$R^{13}{}_I$ can also be the radical —$(CH_2)_e$—$R^{14}{}_I$, where e is an integer, preferably 1, 2 or 3. $R^{14}{}_I$ is a monovalent radical, preferably a saturated or partially unsaturated $C_3$–$C_{10}$-carbocycle.

$R^{13}{}_I$ can further be the monvalent radical —[$CH_2$—CH=C($CH_3$)—$CH_2$]$_f$—H, where f is an integer, preferably 1, 2, 3 or 4.

$R^{13}{}_I$ can also be the radical —[$CH_2$—$CH_2$—O]$_g$—$CH_3$, where g is an integer, preferably in the range from 1 to about 5.

$R^{13}{}_I$ can also be the radical —$(CH_2)_h$-aryl or —$(CH_2)_h$-heteroaryl, where aryl and heteroaryl can also be substituted and, along with their preferred substituents, can be selected from the group listed for $R^2{}_I$. h is an integer, preferably 0, 1, 2 or 3.

$R^{13}{}_I$ can further be the radical —$(CH_2)_b$—$W_I$—$R^5{}_I$. b, $W_I$ and $R^5{}_I$ can each be selected from among the options described for Formula $IV_I$.

Another subclass of compounds of this invention includes peptides of Formula I in which L is an aminoxy group of the formula —O—-N($R^{15}{}_I$)($R^{16}{}_I$), where $R^{15}{}_I$ and $R^{16}{}_I$ are each a monovalent radical, which can independently be a hydrogen atom, a normal or branched $C_1$–$C_8$-alkyl group, which can be substituted by halogen, preferably fluorine, atoms, a $C_3$–$C_8$-cycloalkyl group, a $C_3$–$C_8$-cycloalkyl-$C_1$–$C_4$-alkyl group, a substituted or unsubstituted aryl or heteroaryl group or a substituted or unsubstituted aryl-$C_1$–$C_4$-alkyl group. Aryl and heteroaryl groups and the preferred substituents thereof can be selected from the options listed for $R^2{}_I$. $R^{16}{}_I$ can be selected from among the options listed for $R^{15}{}_I$. Additionally, $R^{15}{}_I$ and $R^{16}{}_I$ can together form a 5-, 6- or 7-membered heterocycle. The compounds of the present invention further comprise the salts of the compounds described above with physiologically tolerated acids.

Another subclass of compounds of this invention includes peptides of Formula I wherein L is an oximato group of the formula —O—N=C($R^{15}{}_I$)($R^{16}{}_I$), $R^{15}{}_I$ and $R^{16}{}_I$ can be selected from among the options listed above and, additionally, can together form a cyclic system comprising, preferably, from about 3 to about 7 ring atoms. This cyclic system can additionally be fused to one or more aromatic rings. Particularly preferred cyclic systems are shown below.

(a)

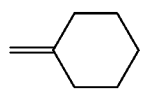

(b)

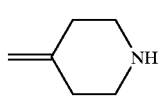

(c)

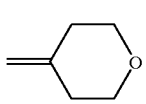

(d)

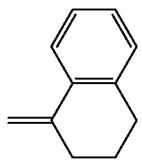

(e)

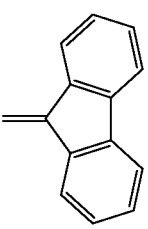

(f)

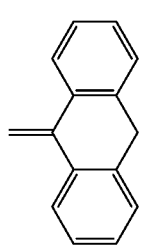

(g)

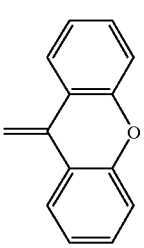

(h)

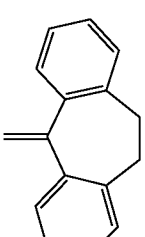

(i)

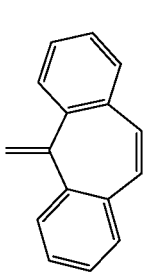

In one embodiment, the invention provides compounds of Formula I wherein A is an amino acid derivative selected from among N-alkyl-D-prolyl, N-alkyl-L-prolyl, N-alkyl-D-piperidine-2-carbonyl, N-alkyl-L-piperidine-2-carbonyl, N,N-dialkyl-D-2-ethyl-2-phenylglycyl and N,N-dialkyl-L-

2-ethyl-2-phenylglycyl, wherein alkyl is methyl, ethyl or isopropyl; and B is a valyl, isoleucyl or 2-t-butyl-L-glycyl residue.

Preferred compounds of the invention include compounds of Formula I wherein r and s are each 0. A is an amino acid derivative selected from among D-N-methyl-piperidine-2-carbonyl, L-N-methyl-piperidine-2-carbonyl, N,N-dimethylamino-isobutyryl, N-methyl-L-prolyl, N-methyl-L-thiazolidine-4-carbonyl, N,N-dimethylglycyl, L-prolyl, L-piperidine-2-carbonyl, N-propyl-D-piperidine-2-carbonyl, D-piperidine-2-carbonyl, N-ethyl-D-piperidine-2-carbonyl, N-methyl-[2,2,5,5-tetramethyl]-L-thiazolidine-2-carbonyl, N-isopropyl-D-piperidine-2-carbonyl, N,N-dimethyl-2-cyclopropylglycyl, N,N-dimethyl-L-2-ethyl-2-phenylglycyl, N,N-dimethyl-D-2-ethyl-2-phenylglycyl, D-prolyl, N-methyl-D-prolyl, N,N-dimethyl-2-(2-fluorophenyl)glycyl, 1-aza-[3,3,0]bicyclooctyl-5-carbonyl, N,N-dimethyl-2-[4-fluoro]phenyl-glycyl, N-methyl-[2,2,5,5-tetramethyl]-thiazolidine-2-carbonyl, 2-(R,S)-ethyl-2-phenylglycyl, D,L-1-aminoindane-1-carbonyl, N,N-dimethyl-2-(R,S)-methyl-2-phenylglycyl, 2-[N,N-dimethylamino]indane-2-carbonyl, 5-[N,N-dimethylamino]-5,6,7,8-tetrahydro-naphthalene-5-carbonyl, N-isopropyl-2-(R,S)-ethyl-2-phenylglycyl, 1-[N,N-dimethylamino]indane-2-carbonyl, N,N-dimethyl-2-propyl-2-phenylglycyl, N,N-dimethyl-2-[4-methoxy]phenyl-glycyl, N-methyl-3-hydroxy-D,L-valyl, N,N-dimethyl-D,L-2-isopropyl-2-phenylglycyl, N-methylpiperidine-2-carbonyl, N-methyl-L-prolyl, N-methyl-1,2,3,4-tetrahydroisoquinoline-1-carbonyl, N-methylazetidine-2-carbonyl, N-isopropylazetidine-2-carbonyl, N,N-dimethyl-[O-methyl]seryl, N,N-dimethyl-[O-methyl]threonyl, N-methyl-1,2,3,4-tetrahydroisoquinoline-3-carbonyl, 1-[N,N-dimethylamino]cyclohexyl-1-carbonyl, 1-[N,N-dimethylamino]cyclopentyl-1-carbonyl and 1,2,3,4-tetrahydroisoquinoline-3-carbonyl. B is valyl, isoleucyl or 2-tert-butylglycyl. D is N-methylvalyl, N-methyl-2-t-butylglycyl or N-methylisoleucyl. E and F are each, independently, prolyl, thiaprolyl, homoprolyl, hydroxyprolyl, 3,4-didehydroprolyl, 4-fluoroprolyl, and 3-methylprolyl. L is an alkoxy group or an amino group of the formula $R^1_f$—N—$R^2_f$, wherein $R^1_f$ and $R^2_f$ are independently selected from the group consisting of hydrogen, alkoxy, hydroxy, alkyl and alkylaryl.

In a particularly preferred subset of the compounds of the invention, r and s are each 0. A is an amino acid derivative selected from among D-N-methyl-piperidine-2-carbonyl, N-ethyl-D-piperidine-2-carbonyl, N-isopropyl-D-piperidine-2-carbonyl, N,N-dimethyl-2-cyclopropyl-glycyl, N-methyl-D-prolyl, 1-aza-[3,3,0]bicyclooctyl-5-carbonyl, N-methyl-[2,2,5,5-tetramethyl]-thiazolidine-2-carbonyl, 2-(R,S)-ethyl-2-phenylglycyl, D,L-1-aminoindane-1-carbonyl, N,N-dimethyl-2-(R,S)-methyl-2-phenylglycyl, 5-[N,N-dimethylamino]-5,6,7,8-tetrahydro- naphthalene-5-carbonyl, 1-[N,N-dimethylamino]indane-2-carbonyl, N,N-dimethyl-2-propyl-2-phenylglycyl, N,N-dimethyl-L-2-ethyl-2-phenylglycyl, N,N-dimethyl-D-2-ethyl-2-phenylglycyl, N-methyl-3-hydroxy-D,L-valyl, N,N-dimethyl-D,L-2-isopropyl-2-phenylglycyl, N-methyl-piperidine-2-carbonyl, N-methyl-D,L-prolyl, N-methyl-1,2,3,4-tetrahydroisoquinoline-1-carbonyl, N-methylazetidine-2-carbonyl, N-isopropylazetidine-2-carbonyl, N,N-dimethyl-[O-methyl]seryl, 1-[N,N-dimethylamino]cyclohexyl-1-carbonyl and 1-[N,N-dimethylamino]cyclopentyl-1-carbonyl. B is valyl; D is N-methylvalyl; and E and F are each prolyl. L is a $C_1$–$C_6$-alkoxy group or an amino group of the formula $R^1_f$—N—$R^2_f$, wherein $R^1_f$ and $R^2_f$ are each independently selected from the group consisting of hydrogen, $C_1$–$C_6$-alkoxy, hydroxy, normal, cyclic or branched $C_1$–$C_{12}$-alkyl, and phenylalkyl.

Synthetic Methods

The compounds of the present invention can be prepared by known methods of peptide synthesis. Thus, the peptides can be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments in turn can be obtained by sequential assembly from amino acids or by fragment coupling of still shorter peptides.

In both sequential assembly and fragment coupling it is necessary to link the units by forming an amide linkage, which can be accomplished via a variety of enzymatic and chemical methods. Chemical methods for forming the amide linkage are described in detail in standard references on peptide chemistry, including Muller, *Methoden der organischen Chemie* Vol. XV/2, 1–364, Thieme Verlag, Stuttgart, (1974); Stewart and Young, *Solid Phase Peptide Synthesis*, 31–34 and 71–82, Pierce Chemical Company, Rockford, Ill. (1984); Bodanszky et al., *Peptide Synthesis*, 85–128, John Wiley & Sons, New York, (1976). Preferred methods include the azide method, the symmetric and mixed anhydride method, the use of in situ generated or preformed active esters, the use of urethane protected N-carboxy anhydrides of amino acids and the formation of the amide linkage using coupling reagents, such as carboxylic acid activators, especially dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl)carbodiimide hydrochloride (EDCI), n-propanephosphonic anhydride (PPA), N,N-bis(2-oxo-oxazolidinyl)amidophosphoryl chloride (BOP—Cl), bromo-tris(pyrrolidino)phosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), O-azabenzotriazolyl-N, N,N',N'-tetramethyluronium salts (HATU), diethylphosphoryl cyanide (DEPCN), 2,5-diphenyl-2,3-dihydro-3-oxo-4-hydroxythiophene dioxide (Steglich's reagent; HOTDO), and 1,1'-carbonyldiimidazole (CDI). The coupling reagents can be employed alone or in combination with additives such as N,N-dimethyl-4-aminopyridine (DMAP), N-hydroxy-benzotriazole (HOBt), N-hydroxyazabenzotriazole (HOAt), N-hydroxybenzotriazine (HOOBt), N-hydroxysuccinimide (HOSu) or 2-hydroxypyridine.

Although the use of protecting groups is generally not necessary in enzymatic peptide synthesis, reversible protection of reactive groups not involved in formation of the amide linkage is necessary for both reactants in chemical synthesis. Three conventional protective group techniques are preferred for chemical peptide synthesis: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, *Methoden der organischen Chemie* Vol. XV/1, pp 20–906, Thieme Verlag, Stuttgart (1974). The units employed for assembling the peptide chain can be reacted in solution, in suspension or by a method similar to that described by Merrifield, *J. Am. Chem. Soc.* 85: (1963) 2149.

Solvents suitable for peptide synthesis include any solvent which is inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of these solvents.

Peptide synthesis on the polymeric support can be carried out in a suitable inert organic solvent in which the amino acid derivatives starting materials are soluble. However, preferred solvents additionally have resin- swelling properties, such as DMF, DCM, NMP, acetonitrile and DMSO, and mixtures of these solvents. Following synthesis, the peptide is removed from the polymeric support. The conditions under which this cleavage is accomplished for various resin types are disclosed in the literature. The cleavage reactions most commonly used are acid- or palladium-catalyzed, the former being conducted in, for example, liquid anhydrous hydrogen fluoride, anhydrous trifluoromethanesulfonic acid, dilute or concentrated trifluoroacetic acid, and acetic acid/dichloromethane/trifluoroethanol mixtures. The latter can be carried out in THF or THF-DCM-mixtures in the presence of a weak base, such as morpholine. Certain protecting groups are also cleaved off under these conditions.

Partial deprotection of the peptide may also be necessary prior to certain derivatization reactions. For example, peptides dialkylated at the N-terminus can be prepared by coupling the appropriate N,N-di-alkylamino acid to the peptide in solution or on the polymeric support, by reductive alkylation of the resin-bound peptide in DMF/1% acetic acid with NaCNBH$_3$ and the appropriate aldehyde or by hydrogenation of the peptide in solution in the presence of the appropriate aldehyde or ketone and Pd/carbon.

The various non-naturally occurring amino acids as well as the various non-amino acid moieties disclosed herein can be obtained from commercial sources or synthesized from commercially available staring materials using methods known in the art. For example, amino acid building blocks with $R^1$ and $R^2$ groups can be prepared according to the method described by Wuensch and Weyl, *Methoden der Organische Chemie,* vol. XV, Springer Verlag: Stuttgart, p. 306 (1974) and references cited therein.

Methods of Use of the claimed Compounds

In another embodiment, the present invention comprises a method for partially or totally inhibiting formation of, or otherwise treating (e.g., reversing or inhibiting the further development of) solid tumors (e.g., tumors of the lung, breast, colon, prostate, bladder, rectum, or endometrial tumors) or hematological malignancies (e.g., leukemias, lymphomas) in a mammal, for example, a human, by administering to the mammal a therapeutically effective amount of a compound or a combination of compounds of Formula I. The compound(s) may be administered alone or in a pharmaceutical composition comprising the compound(s) and an acceptable carrier or diluent. Administration can be by any of the means which are conventional for pharmaceutical, preferably oncological, agents, including oral and parenteral means, such as subcutaneously, intravenously, intramuscularly and intraperitoneally, nasally or rectally. The compounds may be administered alone or in the form of pharmaceutical compositions containing a compound or compounds of Formula I together with a pharmaceutically accepted carrier appropriate for the desired route of administration. Such pharmaceutical compositions may be combination products, i.e., they may also contain other therapeutically active ingredients.

The dosage to be administered to the mammal, such as a human, will contain a therapeutically effective amount of a compound described herein. As used herein, "therapeutically effective amount" is an amount sufficient to inhibit (partially or totally) formation of a tumor or a hematological malignancy or to reverse development of a solid tumor or other malignancy or prevent or reduce its further progression. For a particular condition or method of treatment, the dosage is determined empirically, using known methods, and will depend upon factors such as the biological activity of the particular compound employed; the means of administration; the age, health and body weight of the recipient; the nature and extent of the symptoms; the frequency of treatment; the administration of other therapies; and the effect desired. A typical daily dose will be from about 0.05 to about 50 milligrams per kilogram of body weight by oral administration and from about 0.01 to about 20 milligrams per kilogram of body weight by parenteral administration.

The compounds of the present invention can be administered in conventional solid or liquid pharmaceutical administration forms, for example, uncoated or (film-) coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sucker et al.: *Pharmazeutische Technologie,* Thieme-Verlag, Stuttgart, 1978). The administration forms obtained in this way typically contain from about 1 to about 90% by weight of the active substance.

The present invention will now be illustrated by the following examples, which are not limiting.

EXAMPLES

The proteinogenous amino acids are abbreviated in the examples using the known three-letter code. Other abbreviations employed are: TFA=trifluoroacetic acid, Ac=acetic acid, DCM=dichloromethane, DMSO=dimethylsulfoxide, Bu=butyl, Et=ethyl, Me=methyl, Bzl=benzyl. In the compounds listed, all proteinogenous amino acids are L-amino acids unless otherwise noted. Other abbreviations used: Me$_2$Val=N,N-dimethylvaline, MeVal=N-methylvaline, Bn=benzyl, Me$_2$Aib=[2-N,N-dimethylamino]-isobutyric acid.

General Procedures

The peptides of the invention are synthesized either by classical solution synthesis using standard Z- and Boc-methodology as described above or by standard methods of solid-phase synthesis using Boc and Fmoc protective group techniques.

In the case of solid phase synthesis, the N,N-dialkyl-penta- or hexapeptide acids are liberated from the solid support and further coupled with the corresponding C-terminal amines in solution. BOP—Cl and PyBrop were used as reagents for coupling of the amino acid following the N-methylamino acids. The reaction times were correspondingly increased. For reductive alkylation of the N-terminus, the peptide-resin was deprotected at the N terminus and then reacted with a 3-fold molar excess of aldehyde or ketone in DMF/1% acetic acid with addition of 3 equivalents of NaCNBH$_3$. After the reaction was complete (negative Kaiser test) the resin was washed several times with water, isopropanol, DMF and dichloromethane.

In solution synthesis, the use of either Boc-protected amino acid NCAs (N-tert.-butyloxycarbonyl-amino acid-N-carboxy-anhydrides), Z-protected amino acid NCAs (N-benzyloxycarbonyl-amino acid-N-carboxy-anhydrides), or the use of pivaloyl chloride as condensing agent respectively is most advantageous for coupling of the amino acid following the N-methylamino acids. Reductive alkylation of the N terminus can e.g. be achieved by reaction of the N-terminally deprotected peptides or amino acids with the corresponding aldehydes or ketones using $NaCNBH_3$ or hydrogen-Pd/C.

Valyl-N-methylvalyl-prolyl-prolylbenzylamide hydrochloride for example was prepared according to methods disclosed in German Patent Application No. DE 19527575 A1.

Purification and characterization of the peptides

Peptide purification was carried out by gel chromatography (SEPHADEX G-10, G-15/10% HOAc, SEPHADEX $LH_2O$/MeOH), medium pressure chromatography (stationary phase: HD-SIL C-18, 20–45 micron, 100 Angstrom; mobile phase: gradient with A=0.1% TFA/ MeOH, B=0.1% TFA/water), preparative HPLC (stationary phase: Waters Delta-Pak C-18, 15 micron, 100 Angstrom; mobile phase: gradient with A=0.1% TFA/MeOH, B=0.1% TFA/water), or by crystallization.

The purity of the resulting products was determined by analytical HPLC (stationary phase: 100 2.1 mm VYDAC C-18, 5 micron, 300 A; mobile phase: acetonitrile-water gradient, buffered with 0.1% TFA, 40° C.; or 3.9 mm VYDAC C-18, 30° C.).

Characterization was by fast atom bombardment mass spectroscopy and NMR-spectroscopy.

Example 1

Synthesis of [N-Methyl-L-piperidine-2-carbonyl]-Val-MeVal -Pro-Pro-NHBn (Compound 1) and [N-Methyl-D-piperidine-2-carbonyl]-Val-MeVal -Pro-Pro-NHBn (Compound 2)

Preparation of N-methyl-piperidine-2-carboxylic acid

N-Methyl-piperidine-2-carboxylic acid ethyl ester (5.1 g) was dissolved in a mixture of 100 ml methanol and 10 ml water. NaOH (8 g) was added and the reaction mixture was stirred at room temperature overnight. The solution was then neutralized with hydrochloric acid, evaporated to dryness, and evaporated four times with toluene. The resulting powdery residue was used directly in the next step.

Preparation of [N-Methyl-piperidine-2-carbonyl]-Val-MeVal-Pro-Pro-NHBn

The residue prepared as described above (5.05 g) and H-Val-MeVal-Pro-Pro-NHBn×HCl (4.88 g) were dissolved in 50 ml dry DMF. After cooling the solution in an ice bath, 1.52 g DEPCN and 2.66 ml triethylamine were added. The reaction mixture was stirred at 0° C. for 2 h and then at room temperature overnight. The DMF was removed by evaporation under reduced pressure. The residue was diluted with dichloromethane and the organic phase was washed with aqueous hydrochloric acid (pH 2) and water, dried over sodium sulfate and evaporated to dryness. The diastereomeric mixture was then separated by flash chromatography with a gradient using heptane/ethyl acetate and dichloromethane/methanol. Under the HPLC conditions described in the previous section (C-18 reverse phase) isomer 1 has a retention time of 14.9 minutes, and isomer 2 has a retention time of 15.8 minutes. Both isomers were characterized by fast atom bombardment mass spectrometry ([M+H]+=639).

Example 2

Preparation of $Me_2$Aib-Val-MeVal-Pro-Pro-NHBn (Compound 3)

Preparation of 2-[N,N-dimethylamino]-isobutyric acid

2-Amino-isobutyric acid (10.3 g) was dissolved in 200 ml methanol. After addition of 25 ml aqueous formaldehyde and 1 g 10% Pd/C, the reaction mixture was hydrogenated overnight at room temperature. The catalyst was filtered, and the filtrate was evaporated to dryness. The residue was crystallized from isopropanol to give 4.8 g of the desired product.

Preparation of $Me_2$Aib-Val-MeVal-Pro-Pro-NHBn×HCl

2-[N,N-Dimethylamino]-isobutyric acid (1.3 g, 10 mmol) and 5.5 g (10 mmol) H-Val-MeVal-Pro-Pro-NHBn×HCl were dissolved in 50 ml dry DMF. After cooling to 0° C., 1.6 g DEPCN (10 mmol) and 2.9 ml triethylamine were added to the reaction mixture. The resulting mixture was stirred at 0° C. for 2 h and at room temperature overnight. Ice water (50 mL) was then added, and the resulting mixture was extracted twice with diethyl ether. The ether extracts were washed with 1 N NaOH (1×) and aqueous NaCl (3×), then dried over sodium sulfate and evaporated to dryness under reduced pressure. The product was crystallized from 100 ml diethyl ether with HCl/ether, and recrystallized from acetone to give 1.2 g of the desired product, which was characterized by fast atom bombardment mass spectrometry ([M+H]+= 627).

Example 3

Preparation of [N,N-dimethyl-2-ethyl-2-phenylglycyl]-Val-Me Val-Pro-Pro-NHBn×HCl (Compound 4)

Preparation of [N,N-dimethyl-2-ethyl-2-phenylglycyl]-Val-MeVal-Pro-Pro-NHBn×HCl 2.07 g (10 mmol) N,N-Dimethyl-2-ethyl-2-phenylglycine and 5.5 g (10 mmol) H-Val-MeVal-Pro-Pro-NHBn×HCl were dissolved in 100 ml dry DMF. After cooling to 0° C., 1.6 g DEPCN (10 mmol) and 2.9 ml triethylamine were added. The reaction mixture was stirred at 0° C. for 2 h and at room temperature overnight, then worked up as described above. The crude product was crystallized from diethyl ether with HCl/ether to give 4 g of the desired product, which was characterized by fast atom bombardment mass spectrometry ([M+H]+=703).

Example 4

Preparation of [N-Methyl-D-Pro]-Val-MeVal-Pro-Pro-NHBn (Compound 5)

Preparation of Z-D-Pro-Val-MeVal-Pro-Pro-NHBn 3.74 g Z-D-Pro-OH (15 mmol, BACHEM) and 8.25 g H-Val-MeVal-Pro-Pro-NHBn×HCl (15 mmol) were dissolved in 80 ml dry DMF. After cooling to 0° C., 2.4 g DEPCN (2.25 ml, 15 mmol) and 4.2 ml triethylamine (30 mmol) were added. The reaction mixture was stirred at 0° C. for several hours and room temperature overnight, then the DMF was evaporated under reduced pressure. The residue was diluted with ethyl acetate and thoroughly washed with dilute aqueous HCl (pH 2), water, dilute aqueous NaOH (pH 9–10), and water. The organic phase was dried over sodium sulfate and evaporated to dryness to yield 9.2 g of the desired protected pentapeptide.

Preparation of D-Pro-Val-MeVal-Pro-Pro-NHBn×HCl 8.2 g (11 mmol) Z-D-Pro-Val-MeVal-Pro-Pro-NHBn was dissolved in 70 ml methanol. After addition of 0.7 ml concentrated hydrochloric acid and 0.3 g 10% Palladium/charcoal to the solution, the resulting mixture was hydrogenated. Filtration and evaporation of the solvent gave a residue which was dissolved in water, adjusted to pH 2 and extracted twice with ethyl acetate. The aqueous phase was adjusted to pH 9–10 and extracted twice with dichloromethane. The organic extracts were evaporated and the residue was redissolved in diethylether and crystallized by addition of HCl/ether as the hydrochloride salt to give 6.5 g of the desired product.

Preparation of [N-methyl-D-Pro]-Val-MeVal-Pro-Pro-NHBn×HCl 1.94 g (3 mmol) of D-Pro-Val-MeVal-Pro-Pro-NHBn× HCl was dissolved in 30 ml methanol. To this solution was then added 0.3 g 10% Pd/charcoal and 1.5 ml aqueous formaldehyde solution and the reaction mixture was hydrogenated. Following filtration and evaporation of the solvents, the resulting residue was dissolved in water, adjusted to pH 2 and extracted twice with diethyl ether and several additional times with dichloromethane. The aqueous phase was adjusted to pH 9–10 and extracted twice with dichloromethane. The organic extracts were dried over sodium sulfate and evaporated to dryness. The residue was crystallized as the hydrochloride salt to give 0.5 g of the desired product which was characterized by fast atom bombardment mass spectrometry ([M+H]+=625).

The compounds listed in Table 1 were prepared according to the methods described in Examples 1–4. Where compounds are referred to as "isomer 1" or "isomer 2", isomer 1 is the diastereomer with the shorter retention time on the reversed phase analytical HPLC system. Fast atom bombardment-mass spectrometry results for selected compounds are provided in Table 2. The compounds presented in Examples 1–4 and Table 1 correspond to the indicated sequences:

Compounds 1–5, 7, 9, 10, 12–19, 22–44, 46, 47, 49, 50, 54–59, 61–65, 67–108, 119–142, 144, 145, 147, 148, 150, 151, 153, 154, 156, 157, 159, 160, 162, 163, 165, 166, 168, 169: SEQ ID NO: 1;
Compounds 170–175: SEQ ID NO: 2;
Compounds 6, 8, 20, 45, 48, 51–53, 60, 66, 109–118, 143, 146, 149, 152, 155, 158, 161, 164, 167, 170, 173: SEQ ID NO.: 3;
Compound 11: SEQ ID NO.: 4;
Compound 21: SEQ ID NO.: 5.

TABLE 1

| Compound No. | | | | | |
|---|---|---|---|---|---|
| 6 | Xah | Val | Xaa | Pro | Xab |
| 7 | Xai | Val | Xaa | Pro | Xab |
| 8 | Xae | Val | Xaa | Pro | Xab |
| 9 | Xad | Val | Xaa | Pro | Xbr |
| 10 | Xam | Val | Xaa | Pro | Xab |
| 11 | Xaw | Ile | Xaa | Pro | Xbx |
| 12 | Xao | Val | Xaa | Pro | Xab |
| 13 | Xad | Val | Xaa | Pro | Xap |
| 14 | Xaq | Val | Xaa | Pro | Xab |
| 15 | Xar | Val | Xaa | Pro | Xab |
| 16 | Xas | Val | Xaa | Pro | Xab |
| 17 | Xat | Val | Xaa | Pro | Xab isomer 1 |
| 18 | Xat | Val | Xaa | Pro | Xab isomer 2 |
| 19 | Xaf | Val | Xaa | Pro | Xab |
| 20 | Xav | Val | Xaa | Pro | Xab |
| 21 | Xag | Val | Xaa | Pro | Xab |

TABLE 1-continued

| | | | | | |
|---|---|---|---|---|---|
| 22 | Xax | Val | Xaa | Pro | Xab isomer 1 |
| 23 | Xax | Val | Xaa | Pro | Xab isomer 2 |
| 24 | Xay | Val | Xaa | Pro | Xab |
| 25 | Xaz | Val | Xaa | Pro | Xab isomer 1 |
| 26 | Xaz | Val | Xaa | Pro | Xab isomer 2 |
| 27 | Xba | Val | Xaa | Pro | Xab |
| 28 | Xbb | Val | Xaa | Pro | Xab |
| 29 | Xbc | Val | Xaa | Pro | Xab |
| 30 | Xbd | Val | Xaa | Pro | Xab isomer 1 |
| 31 | Xbd | Val | Xaa | Pro | Xab isomer 2 |
| 32 | Xbe | Val | Xaa | Pro | Xab isomer 1 |
| 33 | Xbe | Val | Xaa | Pro | Xab isomer 2 |
| 34 | Xbf | Val | Xaa | Pro | Xab isomer 1 |
| 35 | Xbg | Val | Xaa | Pro | Xab |
| 36 | Xbh | Val | Xaa | Pro | Xab isomer 1 |
| 37 | Xbh | Val | Xaa | Pro | Xab isomer 2 |
| 38 | Xbi | Val | Xaa | Pro | Xab isomer 1 |
| 39 | Xbi | Val | Xaa | Pro | Xab isomer 2 |
| 40 | Xbk | Val | Xaa | Pro | Xab isomer 1 |
| 41 | Xbk | Val | Xaa | Pro | Xab isomer 2 |
| 42 | Xbl | Val | Xaa | Pro | Xab |
| 43 | Xbf | Val | Xaa | Pro | Xab isomer 2 |
| 44 | Xbm | Val | Xaa | Pro | Xab |
| 45 | Xaw | Val | Xaa | Pro | Xbn |
| 46 | Xbo | Val | Xaa | Pro | Xbn isomer 1 |
| 47 | Xbo | Val | Xaa | Pro | Xbn isomer 2 |
| 48 | Xaw | Val | Xaa | Pro | Xbp |
| 49 | Xbo | Val | Xaa | Pro | Xbp isomer 1 |
| 50 | Xbo | Val | Xaa | Pro | Xbp isomer 2 |
| 51 | Xaw | Val | Xaa | Pro | Xbq |
| 52 | Xaw | Val | Xaa | Pro | Xbr |
| 53 | Xbs | Val | Xaa | Pro | Xbt isomer 1 |
| 54 | Xbl | Val | Xaa | Pro | Xab isomer 1 |
| 55 | Xbl | Val | Xaa | Pro | Xab isomer 2. |
| 56 | Xbu | Val | Xaa | Pro | Xab isomer 1 |
| 57 | Xbv | Val | Xaa | Pro | Xab |
| 58 | Xbw | Val | Xaa | Pro | Xab isomer 1 |
| 59 | Xbw | Val | Xaa | Pro | Xab isomer 2 |
| 60 | Xbs | Val | Xaa | Pro | Xbt isomer 2 |
| 61 | Xbu | Val | Xaa | Pro | Xab isomer 2 |

TABLE 1-continued

| | |
|---|---|
| 62 | Xbo Val Xaa Pro Xbr isomer 1 |
| 63 | Xbo Val Xaa Pro Xbr isomer 2 |
| 64 | Xbo Val Xaa Pro Xbq isomer 1 |
| 65 | Xbo Val Xaa Pro Xbq isomer 2 |
| 66 | Xaw Val Xaa Pro Xbx |
| 67 | Xby Val Xaa Pro Xab |
| 68 | Xbz Val Xaa Pro Xab |
| 69 | Xca Val Xaa Pro Xab isomer 1 |
| 70 | Xca Val Xaa Pro Xab isomer 2 |
| 71 | Xbo Val Xaa Pro Xbx isomer 1 |
| 72 | Xbo Val Xaa Pro Xbx isomer 2 |
| 73 | Xau Val Xaa Pro Xbp |
| 74 | Xau Val Xaa Pro Xbx |
| 75 | Xbi Val Xaa Pro Xbx isomer 2 |
| 76 | Xau Val Xaa Pro Xab isomer 1 |
| 77 | Xau Val Xaa Pro Xab isomer 2 |
| 78 | Xau Val Xaa Pro Xcb |
| 79 | Xbi Val Xaa Pro Xcb isomer 1 |
| 80 | Xbi Val Xaa Pro Xcb isomer 2 |
| 81 | Xbi Val Xaa Pro Xcc isomer 1 |
| 82 | Xbi Val Xaa Pro Xcc isomer 2 |
| 83 | Xbi Val Xaa Pro Xcd |
| 84 | Xbk Val Xaa Pro Xcc isomer 1 |
| 85 | Xbk Val Xaa Pro Xcc isomer 2 |
| 86 | Xax Val Xaa Pro Xbp isomer 1 |
| 87 | Xax Val Xaa Pro Xbp isomer 2 |
| 88 | Xbk Val Xaa Pro Xcb isomer 1 |
| 89 | Xbk Val Xaa Pro Xcb isomer 2 |
| 90 | Xau Val Xaa Pro Xcc |
| 91 | Xau Val Xaa Pro Xcd |
| 92 | Xba Val Xaa Pro Xcb isomer 1 |
| 93 | Xba Val Xaa Pro Xcb isomer 2 |
| 94 | Xbo Val Xaa Pro Xbp isomer 1 |
| 95 | Xbo Val Xaa Pro Xbp isomer 2 |
| 96 | Xau Val Xaa Pro Xbp isomer 1 |
| 97 | Xau Val Xaa Pro Xbp isomer 2 |
| 98 | Xbi Val Xaa Pro Xcd isomer 2 |
| 99 | Xbk Val Xaa Pro Xcd |
| 100 | Xba Val Xaa Pro Xbp isomer 1 |
| 101 | Xba Val Xaa Pro Xbp isomer 2 |
| 102 | Xba Val Xaa Pro Xcc isomer 1 |
| 103 | Xba Val Xaa Pro Xcc isomer 2 |
| 104 | Xba Val Xaa Pro Xcd |
| 105 | Xce Val Xaa Pro Xab |
| 106 | Xcf Val Xaa Pro Xab |
| 107 | Xcg Val Xaa Pro Xab isomer 1 |
| 108 | Xcg Val Xaa Pro Xab isomer 2 |
| 109 | Xaw Val Xaa Pro Xch |
| 110 | Xaw Val Xaa Pro Xci |
| 111 | Xaw Val Xaa Pro Xck |
| 112 | Xaw Val Xaa Pro Xcl |
| 113 | Xaw Val Xaa Pro Xcm |
| 114 | Xaw Val Xaa Pro Xcn |
| 115 | Xaw Val Xaa Pro Xco |
| 116 | Xaw Val Xaa Pro Xcp |
| 117 | Xaw Val Xaa Pro Xcq |
| 118 | Xaw Val Xaa Pro Xcr |
| 119 | Xad Val Xaa Pro Xch |
| 120 | Xad Val Xaa Prb Xci |
| 121 | Xad Val Xaa Pro Xck |
| 122 | Xad Val Xaa Pro Xcl |
| 123 | Xad Val Xaa Pro Xcm |
| 124 | Xad Val Xaa Pro Xcn |
| 125 | Xad Val Xaa Pro Xco |
| 126 | Xad Val Xaa Pro Xcp |
| 127 | Xad Val Xaa Pro Xcq |
| 128 | Xad Val Xaa Pro Xcr |
| 129 | Xad Val Xaa Pro Xbx |
| 130 | Xau Val Xaa Pro Xch |
| 131 | Xau Val Xaa Pro Xci |
| 132 | Xau Val Xaa Pro Xck |
| 133 | Xau Val Xaa Pro Xcl |
| 134 | Xau Val Xaa Pro Xcm |
| 135 | Xau Val Xaa Pro Xcn |
| 136 | Xau Val Xaa Pro Xco |
| 137 | Xau Val Xaa Pro Xcp |
| 138 | Xau Val Xaa Pro Xcq |
| 139 | Xau Val Xaa Pro Xcr |
| 140 | Xau Val Xaa Pro Xbr |

TABLE 1-continued

| | | | | |
|---|---|---|---|---|
| 141 | Xad | Val Xaa Xal Xbx | | |
| 142 | Xau | Val Xaa Xal Xbx | | |
| 143 | Xaw | Val Xaa Xal Xbx | | |
| 144 | Xad | Val Xaa Xal Xch | | |
| 145 | Xau | Val Xaa Xal Xch | | |
| 146 | Xaw | Val Xaa Xal Xch | | |
| 147 | Xad | Val Xaa Xal Xcr | | |
| 148 | Xau | Val Xaa Xal Xcr | | |
| 149 | Xaw | Val Xaa Xal Xcr | | |
| 150 | Xad | Val Xaa Xan Xbx | | |
| 151 | Xau | Val Xaa Xan Xbx | | |
| 152 | Xaw | Val Xaa Xan Xbx | | |
| 153 | Xad | Val Xaa Xan Xch | | |
| 154 | Xau | Val Xaa Xan Xch | | |
| 155 | Xaw | Val Xaa Xan Xch | | |
| 156 | Xad | Val Xaa Xan Xcr | | |
| 157 | Xau | Val Xaa Xan Xar | | |
| 158 | Xaw | Val Xaa Xan Xcr | | |
| 159 | Xau | Ile Xaa Pro Xbx | | |
| 160 | Xad | Ile Xaa Pro Xbx | | |
| 161 | Xaw | Ile Xaa Pro Xch | | |
| 162 | Xad | Ile Xaa Pro Xch | | |
| 163 | Xau | Ile Xaa Pro Xah | | |
| 164 | Xaw | Xcs Xaa Pro Xch | | |
| 165 | Xad | Xcs Xaa Pro Xch | | |
| 166 | Xau | Xcs Xaa Pro Xch | | |
| 167 | Xaw | Xcs Xaa Pro Xbx | | |
| 168 | Xad | Xcs Xaa Pro Xbx | | |
| 169 | Xau | Xcs Xaa Pro Xbx | | |
| 170 | Xaw | Val Xct Pro Xch | | |
| 171 | Xad | Val Xct Pro Xch | | |
| 172 | Xau | Val Xct Pro Xch | | |
| 173 | Xaw | Val Xct Pro Xbx | | |
| 174 | Xad | Val Xct Pro Xbx | | |
| 175 | Xau | Val Xct Pro Xbx | | |

Xaa: N-methyl-valine
Xab: Prolyl N-benzylamide
Xac: L-N-methyl-piperidine-2-carboxylic acid
Xad: D-N-methyl-piperidine-2-carboxylic acid
Xae: N-methyl-L-proline
Xaf: N-methyl-L-thiazolidine-4-carboxylic acid
Xag: N,N-dimethylglycine
Xah: L-proline
Xai: L-piperidine-2-carboxylic acid
Xak: 2-[N,N-dimethylamino]-isobutyric acid
Xal: L-thiazolidine-4-carboxylic acid
Xam: N-propyl-D-piperidine-2-carboxylic acid
Xan: L-3,4-didehydroproline
Xao: D-piperidine-2-carboxylic acid
Xap: proline tert.butylester
Xaq: N-ethyl-D-piperidine-2-carboxylic acid
Xar: N-methyl-[2,2,5,5-tetramethyl]-L-thiazolidine-2-carboxylic acid
Xas: N-isopropyl-D-piperidine-2-carboxylic acid
Xat: N,N-dimethyl-2-cyclopropyl-glycine
Xau: N,N-dimethyl-2-ethyl-2-phenyl-glycine
Xav: D-proline
Xaw: N-methyl-D-proline
Xax: N,N-dimethyl-2-[2-fluoro]phenyl-glycine
Xay: 1-aza-[3,3,0]bicyclooctyl-5-carboxylic acid
Xaz: N,N-dimethyl-2-[4-fluoro]phenyl-glycine
Xba: N-methyl-[2,2,5,5-tetramethyl]-thiazolidine-2-carboxylic acid
Xbb: 2-(R,S)-ethyl-2-phenyl-glycine
Xbc: D,L-1-aminoindane-1-carboxylic acid
Xbd: N,N-dimethyl-2-(R,S)-methyl-2-phenyl-glycine
Xbe: 2-[N,N-dimethylamino]indane-2-carboxylic acid
Xbf: 5-[N,N-dimethylamino]-5,6,7,8-tetrahydronaphthalene-5-carboxylic acid
Xbg: N-isopropyl-2-(R,S)-ethyl-2-phenyl-glycine
Xbh: 1-[N,N-dimethylamino]indane-2-carboxylic acid
Xbi: N,N-dimethyl-2-propyl-2-phenyl-glycine
Xbk: N,N-dimethyl-2-[4-methoxy]phenyl-glycine
Xbl: N-methyl-3-hydroxy-D,L-valine
Xbm: N,N-dimethyl-D,L-2-isopropyl-2-phenyl-glycine
Xbn: proline-N-methoxy-N-methyl-amide
Xbo: N-methyl-piperidine-2-carboxylic acid
Xbp: proline-isopropylamide
Xbq: proline-isoxazolidinyl
Xbr: proline-N-methoxy-N-benzylamide
Xbs: N-methyl-D,L-proline
Xbt: proline-[5-phenyl]isoxazolidinyl
Xbu: N-methyl-1,2,3,4-tetrahydroisoquinoline-1-carboxylic acid
Xbv: N-methyl-azetidine-2-carboxylic acid
Xbw: N-isopropyl-azetidine-2-carboxylic acid
Xbx: proline-tert-butylamide
Xby: N,N-dimethyl-[O-methyl]serine
Xbz: N,N-dimethyl-[O-methyl]threonine
Xca: N-methyl-1,2,3,4-tetrahydroisoquinoline-3-carboxylic acid
Xcb: proline-pentyl (3) amide
Xcc: proline-(R)-phenethylamide
Xcd: proline-(S)-phenethylamide
Xce: 1-[N,N-dimethylamino]cyclohexyl-1-carboxylic acid
Xcf: 1-[N,N-dimethylamino]cyclopentyl-1-carboxylic acid
Xcg: 1,2,3,4-tetrahydroisoquinoline-3-carboxylic acid Xch:

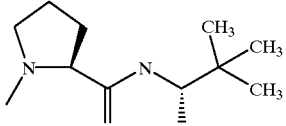

Xci:

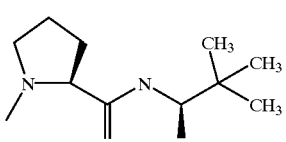

The symbols Xaa in Table 1 represent the following amino acids or residues thereof:

-continued
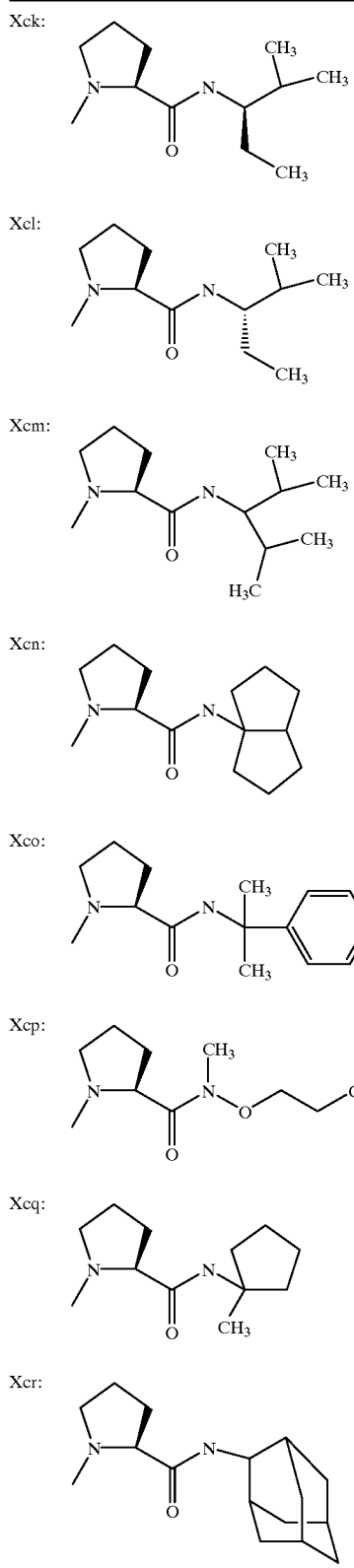
Xcs: L-2-tert-butyl-glycine
Xct: N-methyl-L-Isoleucine
TABLE 2
Results of FAB-MS analysis of selected compounds
| Compound No. | Mol. weight measured |
| --- | --- |
| 1 | 639 |
| 2 | 639 |
| 3 | 627 |
| 4 | 703 |
| 5 | 625 |
| 6 | 611 |
| 7 | 625 |
| 8 | 625 |
| 10 | 667 |
| 12 | 625 |
| 13 | 606 |
| 14 | 653 |
| 15 | 699 |
| 16 | 667 |
| 17 | 639 |
| 18 | 639 |
| 19 | 643 |
| 20 | 611 |
| 21 | 599 |
| 22 | 693 |
| 23 | 693 |
| 24 | 651 |
| 25 | 693 |
| 26 | 693 |
| 27 | 699 |
| 28 | 675 |
| 29 | 673 |
| 30 | 689 |
| 31 | 689 |
| 32 | 701 |
| 33 | 701 |
| 34 | 715 |
| 35 | 717 |
| 36 | 701 |
| 37 | 701 |
| 38 | 717 |
| 39 | 717 |
| 40 | 705 |
| 41 | 705 |
| 42 | 643 |
| 43 | 715 |
| 44 | 703 |
| 45 | 579 |
| 46 | 593 |
| 47 | 593 |
| 48 | 577 |
| 49 | 591 |
| 50 | 591 |
| 51 | 591 |
| 52 | 655 |
| 53 | 667 |
| 54 | 657 |
| 55 | 657 |
| 56 | 687 |
| 57 | 611 |
| 58 | 639 |
| 59 | 639 |
| 60 | 667 |
| 61 | 687 |
| 62 | 669 |
| 63 | 669 |
| 64 | 605 |
| 65 | 605 |
| 66 | 591 |
| 67 | 643 |
| 68 | 657 |
| 69 | 687 |
| 70 | 687 |
| 71 | 605 |
| 72 | 605 |
| 73 | 655 |
| 74 | 669 |
| 75 | 683 |
| 76 | 703 |

TABLE 2-continued

Results of FAB-MS analysis of selected compounds

| Compound No. | Mol. weight measured |
|---|---|
| 77 | 703 |
| 78 | 683 |
| 79 | 697 |
| 80 | 697 |
| 81 | 731 |
| 82 | 731 |
| 83 | 731 |
| 84 | 719 |
| 85 | 719 |
| 86 | 645 |
| 87 | 645 |
| 88 | 685 |
| 89 | 685 |
| 90 | 717 |
| 91 | 717 |
| 92 | 679 |
| 93 | 679 |
| 94 | 591 |
| 95 | 591 |
| 96 | 655 |
| 97 | 655 |
| 98 | 731 |
| 99 | 719 |
| 100 | 651 |
| 101 | 651 |
| 102 | 713 |
| 103 | 713 |
| 104 | 713 |
| 105 | 666 |
| 106 | 653 |
| 107 | 687 |
| 108 | 687 |

Example 5

Evaluation of Biological Activity

In vitro Methodology

Cytotoxicity was measured using a standard methodology for adherent cell lines, such as the microculture tetrazolium assay (MTT). Details of this assay have been published (Alley, M. C. et al., *Cancer Research* 48: 589–601, (1988)). Exponentially growing cultures of HT-29 colon carcinoma cells were used to make microtiter plate cultures. Cells were seeded at 5000–20,000 cells per well in 96-well plates (in 150 mL of media), and grown overnight at 37° C. Test compounds were added, in 10-fold dilutions varying from $10^{-4}$ M to $10^{-10}$ M. Cells were then incubated for 48 hours. To determine the number of viable cells in each well, the MTT dye was added (50 mL of a 3 mg/mL solution of 3-(4,5-dimethylthiazol-2-yl)-2,5-diphenyltetrazolium bromide in saline). This mixture was incubated at 37° C. for 5 hours, and then 50 mL of 25% SDS, pH 2, was added to each well. After an overnight incubation, the absorbance of each well at 550 nm was read using an ELISA reader. The values for the mean +/−SD of data from replicated wells were calculated, using the formula % T/C (% viable cells treated/control). The concentration of test compound which gives a T/C of 50% growth inhibition was designated as the $IC_{50}$.

Table 3 presents the $IC_{50}$ values determined in the HT-29 assay for a series of compounds of the invention.

TABLE 3

| Compound No. | HT-29 [$IC_{50}$] |
|---|---|
| 1 | $4.7 \times 10^{-6}$ |
| 2 | $6.8 \times 10^{-10}$ |
| 3 | $3.5 \times 10^{-8}$ |
| 4 | $1.2 \times 10^{-9}$ |
| 5 | $5.0 \times 10^{-9}$ |
| 8 | $5.1 \times 10^{-7}$ |
| 10 | $1.3 \times 10^{-7}$ |
| 12 | $3.7 \times 10^{-7}$ |
| 13 | $1.0 \times 10^{-9}$ |
| 14 | $1.5 \times 10^{-9}$ |
| 15 | $1.7 \times 10^{-7}$ |
| 16 | $7.3 \times 10^{-10}$ |
| 17 | $6.3 \times 10^{-8}$ |
| 18 | $8.8 \times 10^{-9}$ |
| 22 | $6.4 \times 10^{-7}$ |
| 24 | $2.8 \times 10^{-8}$ |
| 27 | $3.7 \times 10^{-8}$ |
| 28 | $4.9 \times 10^{-8}$ |
| 29 | $3.6 \times 10^{-8}$ |
| 30 | $6.1 \times 10^{-9}$ |
| 31 | $2.0 \times 10^{-7}$ |
| 32 | $8.5 \times 10^{-7}$ |
| 33 | $1.2 \times 10^{-6}$ |
| 34 | $5.0 \times 10^{-9}$ |
| 35 | $1.4 \times 10^{-7}$ |
| 36 | $6.2 \times 10^{-9}$ |
| 37 | $1.9 \times 10^{-7}$ |
| 38 | $7.3 \times 10^{-7}$ |
| 39 | $2.5 \times 10^{-8}$ |
| 40 | $5.6 \times 10^{-7}$ |
| 41 | $7.3 \times 10^{-6}$ |
| 42 | $3.4 \times 10^{-7}$ |
| 43 | $5.9 \times 10^{-8}$ |
| 44 | $4.8 \times 10^{-8}$ |
| 45 | $5.6 \times 10^{-8}$ |
| 46 | $7.2 \times 10^{-7}$ |
| 47 | $2.3 \times 10^{-8}$ |
| 48 | $2.5 \times 10^{-8}$ |
| 49 | $8.8 \times 10^{-8}$ |
| 50 | $8.9 \times 10^{-8}$ |
| 51 | $4.6 \times 10^{-8}$ |
| 52 | $3.4 \times 10^{-7}$ |
| 53 | $5.0 \times 10^{-9}$ |
| 54 | $4.2 \times 10^{-9}$ |
| 55 | $5.6 \times 10^{-8}$ |
| 57 | $2.5 \times 10^{-8}$ |
| 58 | $6.3 \times 10^{-8}$ |
| 59 | $1.9 \times 10^{-7}$ |
| 60 | $1.8 \times 10^{-9}$ |
| 62 | $9.9 \times 10^{-8}$ |
| 63 | $5.6 \times 10^{-8}$ |
| 64 | $1.7 \times 10^{-6}$ |
| 65 | $9.7 \times 10^{-8}$ |
| 66 | $3.4 \times 10^{-7}$ |
| 67 | $3.4 \times 10^{-7}$ |
| 68 | $4.2 \times 10^{-7}$ |
| 70 | $7.1 \times 10^{-6}$ |
| 72 | $1.2 \times 10^{-7}$ |
| 73 | $1.4 \times 10^{-9}$ |
| 74 | $5.1 \times 10^{-8}$ |
| 75 | $8.5 \times 10^{-7}$ |
| 76 | $2.3 \times 10^{-10}$ |
| 77 | $7.2 \times 10^{-9}$ |
| 78 | $4.3 \times 10^{-9}$ |
| 79 | $1.7 \times 10^{-6}$ |
| 80 | $6.7 \times 10^{-8}$ |
| 81 | $1.3 \times 10^{-7}$ |
| 82 | $1.1 \times 10^{-8}$ |
| 83 | $1.3 \times 10^{-7}$ |
| 84 | $1.2 \times 10^{-6}$ |
| 85 | $9.5 \times 10^{-6}$ |
| 90 | $9.3 \times 10^{-10}$ |
| 91 | $8.3 \times 10^{-10}$ |
| 92 | $1.5 \times 10^{-6}$ |
| 93 | $1.8 \times 10^{-6}$ |
| 94 | $3.0 \times 10^{-6}$ |

TABLE 3-continued

| Compound No. | HT-29 [IC$_{50}$] |
|---|---|
| 95 | 1.1 × 10$^{-8}$ |
| 96 | 1.7 × 10$^{-9}$ |
| 97 | 3.2 × 10$^{-8}$ |
| 98 | 6.0 × 10$^{-9}$ |
| 99 | 3.8 × 10$^{-6}$ |
| 100 | 2.3 × 10$^{-6}$ |
| 101 | 2.1 × 10$^{-6}$ |
| 102 | 1.2 × 10$^{-7}$ |
| 103 | 1.1 × 10$^{-7}$ |
| 104 | 3.5 × 10$^{-6}$ |
| 105 | 1.8 × 10$^{-8}$ |
| 106 | 9.7 × 10$^{-8}$ |
| 108 | 7.1 × 10$^{-6}$ |

In vivo Methodology

Compounds of this invention may be further tested in any of the various preclinical assays for in vivo activity which are indicative of clinical utility. Such assays are conducted with nude mice into which tumor tissue, preferably of human origin, has been transplanted ("xenografted"), as is well known in this field. Test compounds are evaluated for their anti-tumor efficacy following administration to the xenograft-bearing mice.

More specifically, human tumors grown in athymic nude mice can be transplanted into new recipient animals, using tumor fragments which are about 50 mg in size. The day of transplantation is designated as day 0. Six to ten days later, the mice are treated with the test compounds given as an intravenous or intraperitoneal injection, in groups of 5–10 mice at each dose. Compounds are given daily for 5 days, 10 days or 15 days, at doses from 10–100 mg/kg body weight. Tumor diameters and body weights are measured twice weekly. Tumor masses are calculated using the diameters measured with Vernier calipers, and the formula:

(length×width$^2$)/2=mg of tumor weight

Mean tumor weights are then calculated for each treatment group, and T/C values are determined for each group relative to the untreated control tumors.

Equivalents

Those skilled in the art will recognize or be able to ascertain using no more than routine experimentation many equivalents to the specific embodiments of the invention described herein. Such equivalents are intended to be encompassed in the scope of the following claims.

We claim:
1. A compound of the formula

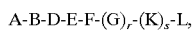

wherein
r and s are each independently, 0 or 1;

A is a proline derivative of Formula II$_a$,

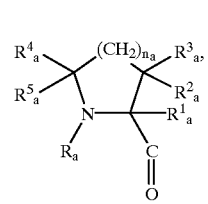

(II$_a$)

wherein n$_a$ is 0 to 3; R$_a$ is hydrogen, or unsubstituted or fluorine-substituted normal, branched or cyclic C$_1$–C$_3$-alkyl; R$^1_a$ is hydrogen, C$_1$–C$_3$-alkyl, phenyl, or substituted phenyl; or R$_a$ and R$^1_a$ together form a propylene bridge; and R$^2_a$, R$^3_a$, R$^4_a$ and R$^5_a$ are each, independently, hydrogen or alkyl; or an α-amino acid derivative of Formula III$_a$,

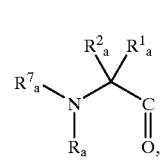

(III$_a$)

wherein R$_a$ is hydrogen or unsubstituted or fluorine-substituted C$_1$–C$_3$-alkyl; R$^1_a$ or C$_1$–C$_4$-alkyl; R$^6_a$ is alkyl, substituted alkyl, alkenyl, phenyl or substituted phenyl; or R$^1_a$ is an alkyl group and R$^6_a$ is C$_1$–C$_6$-alkyl, cycloalkylmethyl, benzyl or substituted benzyl; and R$^7_a$ is hydrogen or alkyl; or an α-amino acid derivative of Formula IV$_a$,

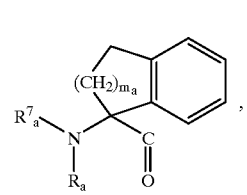

(IV$_a$)

wherein m$_a$ is 1 or 2; R$^7_a$ is hydrogen or alkyl; R$_a$ is hydrogen, or unsubstituted or fluorine-substituted alkyl; or an α-amino acid derivative of Formula V$_a$,

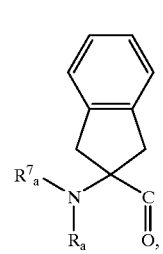

(V$_a$)

wherein R$^7_a$ is hydrogen or alkyl and R$_a$ is hydrogen, or unsubstituted or fluorine-substituted alkyl; or an α-amino acid of Formula VI$_a$,

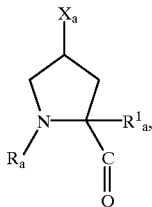
(VI$_a$)

wherein R$_a$ is hydrogen, or unsubstituted or fluorine-substituted alkyl; R$^1_a$ hydrogen, alkyl, phenyl, or substituted phenyl; or R$_a$ and R$^1_a$ together form a propylene bridge; and X$_a$ is hydroxy, alkoxy or fluorine; or an α-amino acid of Formula VII$_a$,

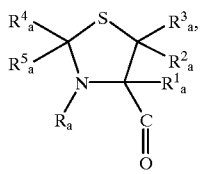
(VII$_a$)

wherein R$_a$ is hydrogen, or unsubstituted or fluorine-substituted alkyl; R$^1_a$ is hydrogen, alkyl, phenyl, or substituted phenyl; or R$_a$ and R$^1_a$ together form a propylene bridge; and R$^2_a$, R$^3_a$, R$^4_a$ and R$^5_a$ are each, independently, hydrogen or alkyl; or an α-amino acid residue of Formula VIII$_a$,

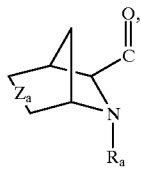
(VIII$_a$)

wherein R$_a$ is hydrogen, or unsubstituted or fluorine-substituted alkyl; or a 2-azabicyclo[2.2.1]heptane-3-carboxylic acid derivative of Formula IX$_a$,

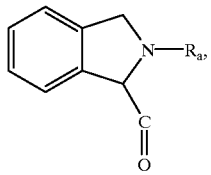
(IX$_a$)

wherein the 3-carbonyl moiety is in the endo or exo position, Z$_a$ is a single bond or a double bond, and R$_a$ is hydrogen or unsubstituted or fluorine-substituted alkyl; or an α-amino acid residue of Formula X$_a$,

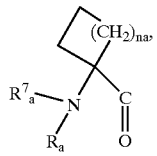
(X$_a$)

wherein n$_a$ is 1, 2 or 3, and R$^7_a$ is hydrogen or alkyl and R$_a$ is hydrogen, unsubstituted alkyl or fluorine-substituted alkyl;

B is a valyl, isoleucyl, allo-isoleucyl, norvalyl, 2-tert-butylglycyl or 2-ethylglycyl residue; or an α-amino acid residue of Formula II$_b$,

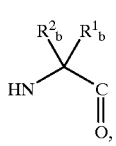
(II$_b$)

wherein R$^1_b$ is hydrogen, and R$^2_b$ is alkyl or alkenyl; or R$^1_b$ and R$^2_b$ together form an isopropylidene group;

D is an N-alkylvalyl, N-alkyl-2-ethylglycyl, N-alkyl-2-tert-butylglycyl, N-alkylnorleucyl, N-alkylisoleucyl, N-alkyl-allo-isoleucyl or N-alkylnorvalyl residue; or an α-amino acid residue of Formula II$_d$,

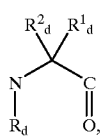
(II$_d$)

wherein R$_d$ is hydrogen, or unsubstituted or fluorine-substituted alkyl; R$^1_d$ is hydrogen; and R$^2_d$ is alkyl, substituted alkyl or alkenyl; or R$^1_d$ and R$^2_d$ together form an isopropylidene group; or an α-amino acid residue of Formula III$_d$,

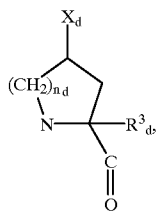
(III$_d$)

wherein n$_d$ is 1 or 2; R$^3_d$ is hydrogen, alkyl or fluorine-substituted alkyl; and X$_d$ is hydrogen; or n$_d$ is 1 and X$_d$ is fluorine, hydroxy, methoxy, or ethoxy;

E is a prolyl, thiazolidinyl-4-carbonyl, homoprolyl,or hydroxyprolyl residue; or an α-amino acid residue of Formula II$_e$,

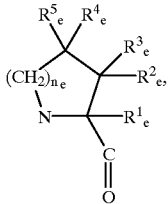
(II$_e$)

wherein n$_e$ is 0, 1 or 2, R$^1_e$ is hydrogen, or unsubstituted or fluorine-substituted alkyl; R$^2_e$ and R$^3_e$ are each, independently, hydrogen or alkyl; R$^4_e$ is hydrogen, hydroxy or alkoxy; and R$^5_e$ is hydrogen or fluorine; or n, is 1 and R$^3_e$ and R$^4_e$ together form a double bond; or n$_e$ is 1 and R$^4_e$ and R$^5_e$ together form a double-bonded oxygen diradical; or n$_e$ is 1 or 2 and R$^1_e$ and R$^2_e$ together form a double bond; or an aminocyclopentanecarboxylic acid residue of Formula III$_e$,

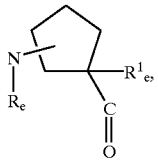
(III$_e$)

wherein R$_e$ is alkyl and R$^1_e$ is hydrogen, or unsubstituted or fluorine-substituted alkyl;

F is a prolyl, thiazolidinyl-4-carbonyl, homoprolyl or hydroxyprolyl residue; or an α-amino acid residue of Formula II$_f$,

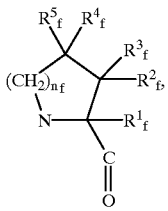
(II$_f$)

wherein n$_f$ is 0, 1 or 2, R$^1_f$ is hydrogen, or unsubstituted or fluorine-substituted alkyl; R$^2_f$ and R$^3_f$ are each, independently, hydrogen or methyl; R$^4_f$ is hydrogen, hydroxy, alkoxy, or fluorine; R$^5_f$ is hydrogen or fluorine; or n$_f$ is 1 and R$^3_f$ and R$^4_f$ together form a double bond; or n$_f$ is 1 and R$^4_f$ and R$^5_f$ together form a double-bonded oxygen diradical; or n$_f$ is 1 or 2 and R$^1_f$ and R$^2_f$ together form a double bond; or a 2- or 3-aminocyclopentanecarboxylic acid residue of Formula III$_f$,

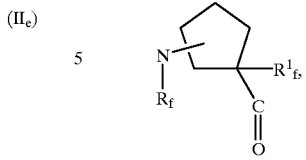
(III$_f$)

wherein R$_f$ is alkyl and R$^1_f$ is hydrogen, or unsubstituted or fluorine-substituted alkyl; or an N-alkylglycyl or N-alkylalanyl residue;

G is an α-amino acid residue of Formula II$_g$,

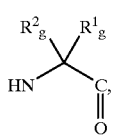
(II$_g$)

wherein R$^1_g$ is hydrogen or alkyl and R$^2_g$ is hydrogen, alkyl, arylalkyl, heteroarylalkyl, phenyl or substituted phenyl; or R$^1_g$ and R$^2_g$, together with the α-carbon atom, form a C$_5$–C$_6$ ring or a benzo-fused C$_5$ ring;

K is an α-amino acid of Formula II$_k$,

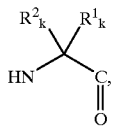
(II$_k$)

wherein R$^1_k$ is hydrogen, or alkyl; and R$^2_k$ is hydrogen, alkyl, arylalkyl, heteroarylalkyl, phenyl or substituted phenyl; or R$^1_g$ and R$^2_g$, together with the α-carbon atom, form a cyclopentane ring or a benzo-fused cyclopentane ring; and L is a substituted or unsubstituted amino, hydrazido, aminoxy or oximato group.

2. The compound of claim 1 wherein A is a proline derivative of Formula II$_a$; R$_a$ is hydrogen, methyl, ethyl, normal propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl; R$^1_a$ is hydrogen, methyl, ethyl, propyl, phenyl, or substituted phenyl, wherein the phenyl substituents comprise one or more alkyl, alkoxy, trifluoromethyl or nitro groups; or R$_a$ and R$^1_a$ together form a propylene bridge; and R$^2_a$, R$^3_a$, R$^4_a$ and R$^5_a$ are each, independently, hydrogen or methyl.

3. The compound of claim 1 wherein A is an α-amino acid residue of Formula III$_a$, wherein R$_a$ is hydrogen, methyl, ethyl, normal propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl; R$^1_a$ is a C$_1$–C$_3$-alkyl group; R$^6_a$ is methoxymethyl, 1-methoxyethyl, vinyl, 1-methylvinyl, 1-trifluoromethylvinyl, 1-trifluoromethylethyl, 1-trifluoromethyl-2,2,2-trifluoroethyl, 1,1-dimethylhydroxymethyl, phenyl or substituted phenyl, wherein the phenyl substituents comprise one or more halogen atoms or one or more C$_1$–C$_4$-alkyl, methoxy, trifluoromethyl or nitro groups; or $R^1_a$ is $C_1$–$C_3$-alkyl and $R^6_a$ is $C_1$–$C_6$-alkyl, cycloalkylmethyl, benzyl or substituted benzyl, wherein the benzyl substituents comprise one or more halogen atoms, or one or more $C_1$–$C_4$-alkyl, methoxy, ethoxy, trifluoromethyl or nitro groups; and $R^7_a$ is methyl, ethyl or isopropyl.

4. The compound of claim 1 wherein A is an α-amino acid residue of Formula $IV_a$, wherein $R^7_a$ is methyl, ethyl or isopropyl; and $R_a$ is hydrogen, methyl, ethyl, n-propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl.

5. The compound of claim 1 wherein A is an α-amino acid residue of Formula $V_a$, wherein $R^7_a$ is methyl, ethyl or isopropyl and $R_a$ is hydrogen, methyl, ethyl, n-propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl.

6. The compound of claim 1 wherein A is an α-amino acid residue of Formula $VI_a$, wherein $R_a$ is hydrogen, methyl, ethyl, normal propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl; $R^1_a$ is hydrogen, methyl, ethyl, propyl, phenyl, or substituted phenyl, wherein the phenyl substituents comprise one or more alkyl, alkoxy, trifluoromethyl or nitro groups; or $R_a$ and $R^1_a$ together form a propylene bridge; and $X_a$ is a hydroxy, methoxy, or ethoxy group, or a fluorine atom.

7. The compound of claim 1 wherein A is an α-amino acid residue of Formula $VII_a$, wherein $R_a$ is hydrogen, methyl, ethyl, n-propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl; $R^1_a$ is hydrogen, methyl, ethyl, propyl, phenyl, or substituted phenyl, wherein the phenyl substituents comprise one or more alkyl, alkoxy, trifluoromethyl or nitro groups; or $R_a$ and $R^1_a$ together form a propylene bridge; and $R^2_a$, $R^3_a$, $R^4_a$ and $R^5_a$ are each, independently, hydrogen or methyl.

8. The compound of claim 1 wherein A is an α-amino acid residue of Formula $VIII_a$, wherein $R_a$ is hydrogen, methyl, ethyl, normal propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl.

9. The compound of claim 1 wherein A is an amino acid residue of Formula $IX_a$, wherein $R_a$ is hydrogen, methyl, ethyl, normal propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl.

10. The compound of claim 1 wherein A is an α-amino acid residue of Formula $X_a$, wherein $R^7_a$ is methyl, ethyl or isopropyl and $R_a$ is hydrogen, methyl, ethyl, normal propyl, isopropyl, cyclopropyl, 2-fluoroethyl, 2,2,2-trifluoroethyl, 1-methyl-2-fluoroethyl, 1-fluoromethyl-2-fluoroethyl, or 1-methyl-2-fluoroethyl.

11. The compound of claim 1 wherein B is a residue of Formula $II_b$, wherein $R^1_b$ is hydrogen and $R^2_b$ is cyclopropyl, n-butyl, isobutyl, tertiary butyl, methoxymethyl, 1-methoxyethyl, or 1-methylvinyl.

12. The compound of claim 1 wherein D is an N-alkylvalyl residue, an N-alkyl-2-ethylglycyl residue, an N-alkyl-2-tert-butylglycyl residue, an N-alkylnorleucyl residue, an N-alkylisoleucyl residue, an N-alkyl-allo-isoleucyl residue or an N-alkylnorvalyl residue, wherein the N-alkyl group is methyl or ethyl.

13. The compound of claim 1 wherein D is an α-amino acid residue of Formula $II_d$, $R^1_d$ is hydrogen and $R^2_d$ is cyclopropyl, methoxymethyl, 1-methoxyethyl, or 1-methylvinyl.

14. The compound of claim 1 wherein D is an α-amino acid residue of Formula $III_d$, wherein $R^3_d$ is hydrogen, methyl, ethyl, normal propyl, isopropyl, cyclopropyl, 2-fluoroethyl, 2,2,2-trifluoroethyl, 1-methyl-2-fluoroethyl, or 1-fluoromethyl-2-fluoroethyl; and $X_d$ is a hydrogen atom; or $n_d$ is 1 and $X_d$ is a fluorine atom, or a hydroxy, methoxy, or ethoxy group.

15. The compound of claim 1 wherein E is an α-amino acid residue of Formula $II_e$, and $R^1_e$ is hydrogen, methyl, ethyl, n-propyl, isopropyl, cyclopropyl, 2-fluoroethyl, 2,2,2,-trifluoroethyl, 1-methyl-2-fluoroethyl, or 1-fluoromethyl-2-fluoroethyl; $R^2_e$ and $R^3_e$ are each, independently, hydrogen or methyl; $R^4_e$ is a hydrogen atom or a hydroxy, methoxy or ethoxy group; and $R^5_e$ is hydrogen or fluorine; or $n_e$ is 1 and $R^3_e$ and $R^4_e$ together form a double bond; or $n_e$ is 1 and $R^4_e$ and $R^5_e$ together form a double-bonded oxygen diradical; or $n_e$ is 1 or 2 and $R^1_e$ and $R^2_e$ together form a double bond.

16. The compound of claim 1 wherein E is an aminocyclopentanecarboxylic acid residue of Formula $III_e$, wherein $R_e$ is methyl or ethyl group and $R^1_e$ is hydrogen, or methyl, ethyl, normal propyl, isopropyl, cyclopropyl, 2-fluoroethyl, 2,2,2,-trifluoroethyl, 1-methyl-2-fluoroethyl, or 1-fluoromethyl-2-fluoroethyl.

17. The compound of claim 1 wherein F is an α-amino acid residue of Formula $II_f$, wherein $R^1_f$ is a hydrogen atom, or methyl, ethyl, normal propyl, isopropyl, cyclopropyl, 2-fluoroethyl, 2,2,2,-trifluoroethyl, 1-methyl-2-fluoroethyl, or 1-fluoromethyl-2-fluoroethyl; $R^2_f$ is a hydrogen atom or a methyl group; $R^3_f$ is a hydrogen atom or a methyl group; $R^4_f$ is a hydrogen atom, a hydroxy, methoxy, ethoxy, or a fluorine atom; $R^5_f$ is a hydrogen atom or a fluorine atom; or $n_f$ is 1 and $R^3_f$ and $R^4_f$ together form a double bond; or $n_f$ is 1 and $R^4_f$ and $R^5_f$ together form a double-bonded oxygen radical; or $n_f$ is 1 or 2 and $R^1_f$ and $R^2_f$ together form a double bond.

18. The compound of claim 1 wherein F is a 2- or 3-aminocyclopentanecarboxylic acid residue of Formula $III_f$, wherein $R_f$ is methyl or ethyl and $R^1_f$ is hydrogen, methyl, ethyl, normal propyl, isopropyl, cyclopropyl, 2-fluoroethyl, 2,2,2,-trifluoroethyl, 1-methyl-2-fluoroethyl, or 1-fluoromethyl-2-fluoroethyl.

19. The compound of claim 1 wherein F is an N-alkylglycyl residue or an N-alkylalanyl residue and the N-alkyl group is methyl or ethyl.

20. The compound of claim 1 wherein G is an α-amino acid residue of Formula $II_g$, wherein $R^1_g$ is hydrogen, methyl, ethyl or n-propyl, and $R^2_g$ is hydrogen, ethyl, isopropyl, tert-butyl, isobutyl, 2-methylpropyl, cyclohexylmethyl, benzyl, thiazolyl-2-methyl, pyridyl-2-methyl, n-butyl, 2,2-dimethylpropyl, naphthylmethyl, n-propyl, phenyl or substituted phenyl, wherein the phenyl substituents are one or more halogen atoms, one or more $C_1$–$C_4$-alkyl, methoxy, ethoxy, nitro or trifluoromethyl groups or a dioxomethylene group.

21. The compound of claim 1 wherein K is an α-amino acid of Formula $II_k$, wherein $R^1_k$ is hydrogen, methyl, ethyl or normal propyl, and $R^2_k$ is hydrogen, ethyl, isopropyl, tert-butyl, isobutyl, 2-methylpropyl, cyclohexylmethyl, benzyl, thiazolyl-2-methyl, pyridyl-2-methyl, normal butyl, 2,2-dimethylpropyl, naphthylmethyl, n-propyl, phenyl or substituted phenyl, wherein the phenyl substituents comprise one or more halogen atoms, or one or more $C_1$–$C_4$-alkyl, methoxy, ethoxy, nitro or trifluoromethyl groups or a dioxomethylene group; or $R^1_g$ and $R^2_g$, together with the α-carbon atom, form a cyclopentane ring or a benzo-fused cyclopentane ring.

22. The compound of claim 1 wherein L is an amino group of Formula II$_l$,

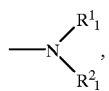     (II$_l$)

wherein

R$^1_l$ is a hydrogen atom, a normal or branched, saturated or unsaturated C$_1$–C$_{18}$-alkoxy group, a substituted or unsubstituted aryloxy group, a substituted or unsubstituted aryl-C$_1$–C$_6$-alkoxy group, a substituted or unsubstituted aryloxy-C$_1$–C$_6$-alkoxy group, wherein the aryl substituents comprise one or more halogen atoms or one or more C$_1$–C$_4$-alkyl, methoxy, ethoxy, trifluoromethyl, dioxymethylene, or nitro groups; or a heteroaryl-C$_1$–C$_6$-alkoxy group; and R$^2_l$ is a hydrogen atom, a normal or branched C$_1$–C$_{18}$-alkyl group, a normal or branched C$_1$–C$_{18}$ alkenyl group, a C$_3$–C$_{10}$-cycloalkyl group, an aryl group or a substituted aryl group, wherein the aryl substituents comprise one or more halogen atoms, or one or more C$_1$–C$_4$-alkyl, methoxy, ethoxy, trifluoromethyl, cyano or nitro groups, a C$_1$–C$_7$-alkoxycarbonyl group, a dioxymethylene group, a C$_1$–C$_7$-alkylsulfonyl group, an amino group or a C$_1$–C$_6$-dialkylamino group; a heteroaryl group or a substituted heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine, wherein the heteroaryl substituents comprise one or more C$_1$–C$_6$-alkyl, hydroxyl or phenyl groups.

23. The compound of claim 22 wherein R$^2_l$ is of Formula II$_r$,

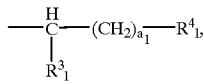     (II$_r$)

wherein a$_l$ is 0, 1, 2, 3, 4, or 5; R$^3_l$ is methyl, ethyl, normal propyl or isopropyl; and R$^4_l$ is a saturated or partially unsaturated carbocyclic system comprising from about 3 to about 10 carbon atoms, an aryl group or a substituted aryl group, wherein the aryl substituents comprise one or more halogen atoms, or one or more C$_1$–C$_4$-alkyl groups, methoxy, ethoxy, trifluoromethyl, cyano or nitro groups, a C$_1$–C$_7$-alkoxycarbonyl group, a dioxymethylene group, a C$_1$–C$_7$-alkylsulfonyl group, an amino group or a C$_1$–C$_6$-dialkylamino group; a heteroaryl group or a substituted heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine, wherein the heteroaryl substituents comprise one or more C$_1$–C$_6$-alkyl, hydroxyl or phenyl groups.

24. The compound of claim 22 wherein R$^2_l$ is of Formula III$_r$,

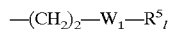     (III$_r$)

wherein

W$_l$ is an N(R$^6_l$) group, an oxygen atom or a sulfur atom;

R$^5_l$ and R$^6_l$ are each, independently, a hydrogen atom or a C$_1$–C$_4$-alkyl, C$_3$–C$_7$-cycloalkyl, aryl, arylmethyl, substituted aryl, or substituted arylmethyl group, wherein the aryl substituents comprise one or more halogen atoms, or one or more C$_1$–C$_4$-alkyl groups, methoxy, ethoxy, trifluoromethyl, cyano or nitro groups, a C$_1$–C$_7$-alkoxycarbonyl group, a dioxymethylene group, a C$_1$–C$_7$-alkylsulfonyl group, an amino group or a C$_1$–C$_6$-dialkylamino group; or R$^6_l$ is a C$_1$–C$_{18}$-alkanoyl group or a benzoyl group.

25. The compound of claim 22 wherein R$^2_l$ is a monovalent radical of Formula IV$_r$,

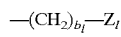     (IV$_r$)

wherein b$_l$ is 2, 3, or 4 and Z$_l$ is a formyl, aminocarbonyl, hydrazinocarbonyl, cyclic acetal, cyclic thioacetal, acyclic acetal or acyclic thioacetal group.

26. The compound of claim 22 wherein R$^2_l$ is of Formula V$_r$,

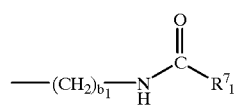     (V$_r$)

wherein b$_l$ is 2, 3, or 4; and

R$^7_l$ is a polyglycol group of the formula —O—(CH$_2$CH$_2$O)$_{d_l}$—CH$_3$, wherein d$_l$ is between about 2 and about 4, or between about 40 and about 90.

27. The compound of claim 22 wherein R$^2_l$ is of Formula VI$_r$,

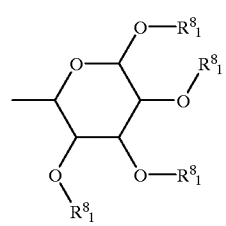     (VI$_r$)

and R$^8_l$ is a hydrogen atom, or a C$_1$–C$_4$ alkanoyl, C$_1$–C$_4$ alkyl, benzoyl, or benzyl group.

28. The compound of claim 1 wherein L is a β-hydroxylamino group of Formula III$_l$,

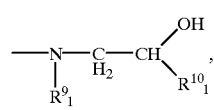     (III$_l$)

wherein

R$^9_l$ is a hydrogen atom, or a C$_1$–C$_6$-alkyl, an aryl group or a substituted aryl group, wherein the aryl substituents comprise one or more halogen atoms, or one or more $C_1$–$C_4$-alkyl groups, methoxy, ethoxy, trifluoromethyl, cyano or nitro groups, a $C_1$–$C_7$-alkoxycarbonyl group, a dioxymethylene group, a $C_1$–$C_7$-alkylsulfonyl group, an amino group or a $C_1$–$C_6$-dialkylamino group; and $R^{10}{}_l$ is a hydrogen atom, a methyl group or a phenyl group.

29. The compound of claim 1 wherein at least one of r and s is 1, and L is an amino group of Formula $IV_l$,

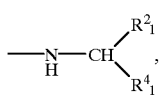

(IV$_l$)

wherein $R^2{}_l$ and $R^4{}_l$ are each, independently, hydrogen or $C_1$–$C_{10}$-alkyl; or $R^2{}_l$, $R^4{}_l$ and the α-carbon together form a $C_5$–$C_6$-carbocycle.

30. The compound of claim 1 wherein L is a hydrazido group of Formula $V_l$,

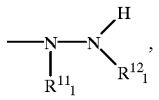

(V$_l$)

wherein $R^{12}{}_l$ is a hydrogen atom, a normal or branched $C_1$–$C_8$-alkyl group, a $C_3$–$C_8$-cycloalkyl group, a $C_3$–$C_8$-cycloalkyl-$C_1$–$C_4$-alkyl group, an aryl group, an aryl-$C_1$–$C_4$-alkyl group, or a substituted aryl or aryl-$C_1$–$C_4$-alkyl group wherein the aryl substituents comprise one or more halogen atoms, or one or more methoxy, ethoxy, trifluoromethyl, dioxymethylene, nitro, cyano, $C_1$–$C_7$-alkoxycarbonyl, $C_1$–$C_7$-alkylsulfonyl, amino, or $C_1$–$C_7$-dialkylamino groups; or a heteroaryl-$C_1$–$C_4$-alkyl group, wherein the heteroaryl group is derived from imidazole, pyrrole, thiophene, furan, thiazole, oxazole, pyrazole, 1,2,4- or 1,2,3-triazole, oxadiazole, thiadiazole, isoxazole, isothiazole, pyrazine, pyridazine, pyrimidine, pyridine, benzofuran, benzothiophene, benzimidazole, benzothiazole, benzopyran, indole, isoindole, indazole or quinoline and the heteroaryl substituents comprise one or more $C_1$–$C_6$-alkyl, hydroxyl or phenyl groups; and $R^{11}{}_l$ is a hydrogen atom; or r is 1, s is 1 or both r and s are 1, and $R^{11}{}_l$ is a normal or branched $C_1$–$C_8$-alkyl group, a $C_3$–$C_8$-cycloalkyl group, a $C_3$–$C_8$-cycloalkyl-$C_1$–$C_4$-alkyl group, an aryl-$C_1$–$C_4$-alkyl group, an aryl group or a substituted aryl-$C_1$–$C_4$-alkyl or aryl group, wherein the aryl substituents comprise one or more halogen atoms, or one or more $C_1$–$C_4$-alkyl groups, methoxy, ethoxy, trifluoromethyl, cyano or nitro groups, a $C_1$–$C_7$-alkoxycarbonyl group, a dioxymethylene group, a $C_1$–$C_7$-alkylsulfonyl group, an amino group or a $C_1$–$C_6$-dialkylamino group; a heteroaryl group a heteroaryl-$C_1$–$C_4$-alkyl group or a substituted heteroaryl or heteroaryl-$C_1$–$C_4$-alkyl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine, wherein the heteroaryl substituents comprise one or more $C_1$–$C_6$-alkyl, hydroxyl or phenyl groups; or $R^{11}{}_l$ and $R^{12}{}_l$ together form a propylene bridge or a butylene bridge.

31. The compound of claim 1 wherein L is a monovalent radical of the formula —W—$R^{13}{}_l$, wherein W is oxygen or sulfur;

$R^{13}{}_l$ is a $C_3$–$C_{10}$-cycloalkyl, straight-chain or branched $C_2$–$C_{16}$-alkenylmethyl, $C_1$–$C_{16}$-alkyl or halogen-substituted $C_1$–$C_{16}$-alkyl group or $R^{13}{}_l$ is a monovalent radical of the formula —$(CH_2)_1$e—$R^{14}{}_l$, e is 1, 2, or 3, and $R^{14}{}_l$ is a saturated or partially unsaturated $C_3$–$C_{10}$-carbocyclic group; or $R^{13}{}_l$ is a monovalent radical of the formula —[$CH_2$—CH=C($CH_3$)—$CH_2$]$_f$—H, and f is 1, 2, 3, or 4; or $R^{13}{}_l$ is a monovalent radical of the formula —[$CH_2$—$CH_2$—O]$_g$—$CH_3$, and g is 1, 2, 3, 4, or 5; or $R^{13}{}_l$ is a monovalent radical of the formula —$(CH_2)_h$—X, wherein h is 0, 1, 2, or 3, X is an aryl group or a substituted aryl group, wherein the aryl substituents comprise one or more halogen atoms, or one or more $C_1$–$C_4$-alkyl groups, methoxy, ethoxy, trifluoromethyl, cyano or nitro groups, a $C_1$–$C_7$-alkoxycarbonyl group, a dioxymethylene group, a $C_1$–$C_7$-alkylsulfonyl group, an amino group or a $C_1$–$C_6$-dialkylamino group; or X is a heteroaryl group or a substituted heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine, wherein the heteroaryl substituents comprise one or more $C_1$–$C_6$-alkyl, hydroxyl or phenyl groups, an aryl-$C_1$–$C_4$-alkyl group or a heteroaryl-$C_1$–$C_4$-alkyl group; or $R^{13}{}_l$ is a monovalent radical of the formula —$(CH_2)_b$—$W_l$—$R^5{}_l$, b is an integer, $W_l$ is an oxygen atom, a sulfur atom, or an $NR^6{}_l$ group, $b_l$ is 2, 3, or 4; $R^5{}_l$ is a saturated or partially unsaturated carbocyclic system which contains from about 3 to about 10 carbon atoms, an aryl or substituted aryl group, wherein the aryl substituents comprise one or more halogen atoms, or one or more $C_1$–$C_4$-alkyl groups, methoxy, ethoxy, trifluoromethyl, cyano or nitro groups, a $C_1$–$C_7$-alkoxycarbonyl group, a dioxymethylene group, a $C_1$–$C_7$-alkylsulfonyl group, an amino group or a $C_1$–$C_6$-dialkylamino group; a heteroaryl group or a substituted heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine, wherein the heteroaryl substituents comprise one or more $C_1$–$C_6$-alkyl, hydroxyl or phenyl groups; $R^6{}_l$ is a hydrogen atom, or a $C_1$–$C_4$-alkyl, $C_3$–$C_7$-cycloalkyl, $C_1$–$C_{18}$-alkanoyl, benzoyl, aryl or arylmethyl group or a substituted aryl or arylmethyl group, wherein the aryl substituents comprise one or more halogen atoms, or one or more $C_1$–$C_4$-alkyl groups, methoxy, ethoxy, trifluoromethyl, cyano or nitro groups, a $C_1$–$C_7$-alkoxycarbonyl group, a dioxymethylene group, a $C_1$–$C_7$-alkylsulfonyl group, an amino group or a $C_1$–$C_6$-dialkylamino group.

32. The compound of claim 1 wherein L is an aminoxy group of the formula —O—N($R^{15}_l$)($R^{16}_l$) wherein $R^{15}_l$ and $R^{16}_l$ are each, independently, a hydrogen atom, a normal or branched $C_1$–$C_8$-alkyl group, a halogen-substituted normal or branched $C_1$–$C_8$-alkyl group, a $C_3$–$C_8$-cycloalkyl group, a $C_3$–$C_8$-cycloalkyl-$C_1$–$C_4$ alkyl group, an aryl group, an aryl-$C_1$–$C_4$-alkyl group or a substituted aryl or aryl-$C_1$–$C_4$-alkyl group, wherein the aryl substituents comprise one or more halogen atoms, or one or more $C_1$–$C_4$-alkyl groups, methoxy, ethoxy, trifluoromethyl, cyano or nitro groups, a $C_1$–$C_7$-alkoxycarbonyl group, a dioxymethylene group, a $C_1$–$C_7$-alkylsulfonyl group, an amino group or a $C_1$–$C_6$-dialkylamino group; a heteroaryl group, a heteroaryl-$C_1$–$C_4$-alkyl group or a substituted heteroaryl or heteroaryl-$C_1$–$C_4$-alkyl group derived from imidazole, isoxazole, isothiazole, thiazole, oxazole, pyrazole, thiophene, furan, pyrrole, 1,2,4- or 1,2,3-triazole, pyrazine, indole, benzofuran, enzothiophene, indole, isoindole, indazole, quinoline, pyridazine, pyrimidine, benzimidazole, benzopyran, benzothiazole, oxadiazole, thiadiazole or pyridine, wherein the heteroaryl substituents comprise one or more $C_1$–$C_6$-alkyl, hydroxyl or phenyl groups; or $R^{15}_l$ and $R^{16}_l$ together with the nitrogen atom form a heterocyclic ring structure comprising 5, 6, or 7 atoms.

33. The compound of claim 1 wherein L is a oximato group of the formula —O—N═C($R^{15}_l$)($R^{16}_l$), wherein $R^{15}_l$ and $R^{16}_l$ are each, independently, a hydrogen atom, a normal or branched $C_1$–$C_8$-alkyl group, a halogen-substituted normal or branched $C_1$–$C_8$-alkyl group, a $C_3$–$C_8$-cycloalkyl group, a $C_3$–$C_8$-cycloalkyl-$C_1$–$C_4$-alkyl group, an aryl group, an aryl-$C_1$–$C_4$-alkyl group or a substituted aryl or aryl-$C_1$–$C_4$-alkyl group, wherein the aryl substituents comprise one or more halogen atoms, or one or more $C_1$–$C_4$-alkyl groups, methoxy, ethoxy, trifluoromethyl, cyano or nitro groups, a $C_1$–$C_7$-alkoxycarbonyl group, a dioxymethylene group, a $C_1$–$C_7$-alkylsulfonyl group, an amino group or a $C_1$–$C_6$-dialkylamino group; a heteroaryl group or a substituted heteroaryl group derived from imidazole, isoxazole, isothiazole, thiazole, oxazole, pyrazole, thiophene, furan, pyrrole, 1,2,4- or 1,2,3-triazole, pyrazine, indole, benzofuran, benzothiophene, indole, isoindole, indazole, quinoline, pyridazine, pyrimidine, benzimidazole, benzopyran, benzothiazole, oxadiazole, thiadiazole or pyridine, wherein the heteroaryl substituents comprise one or more $C_1$–$C_6$-alkyl, hydroxyl or phenyl groups; or $R^{15}_l$ and $R^{16}_l$, together with the carbon atom, form a cyclic system or a cyclic system which is fused to an aromatic ring system.

34. The compound of claim 33 wherein the cyclic system is selected from the group consisting of

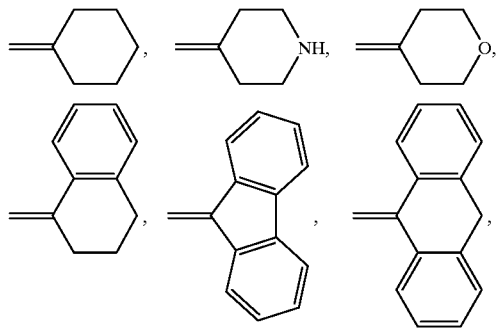

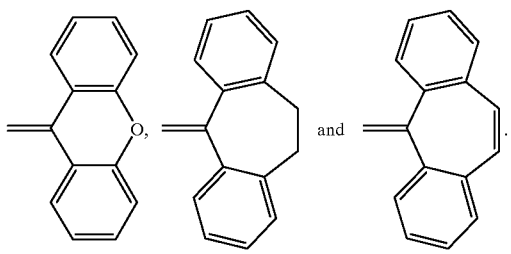

35. The compound of claim 1 wherein
A is an amino acid derivative selected from the group consisting of N-alkyl-D-prolyl, N-alkyl-L-prolyl, N-alkyl-D-piperidine-2-carbonyl, N-alkyl-L-piperidine-2-carbonyl, N,N-dialkyl-D-2-ethyl-2-phenylglycyl and N,N-dialkyl-L-2-ethyl-2-phenylglycyl, wherein alkyl is methyl, ethyl or isopropyl; and
B is valyl, isoleucyl or 2-t-butyl-L-glycyl.

36. A compound of the formula

A-B-D-E-F-L, wherein
A is an amino acid derivative selected from the group consisting of D-N-methyl-piperidine-2-carbonyl, L-N-methyl-piperidine-2-carbonyl, N,N-dimethylamino-isobutyryl, N-methyl-L-prolyl, N-methyl-L-thiazolidine-4-carbonyl, N,N-dimethylglycyl, L-prolyl, L-piperidine-2-carbonyl, N-propyl-D-piperidine-2-carbonyl, D-piperidine-2-carbonyl, N-ethyl-D-piperidine-2-carbonyl, N-methyl-[2,2,5,5-tetramethyl]-L-thiazolidine-2-carbonyl, N-isopropyl-D-piperidine-2-carbonyl, N,N-dimethyl-2-cyclopropylglycyl, N,N-dimethyl-D-2-ethyl-2-phenylglycyl, N, N-dimethyl-L-2-ethyl-2-phenylglycyl, D-prolyl, N-methyl-D-prolyl, N,N-dimethyl-2-(2-fluorophenyl-glycyl, 1-aza-[3,3,0] bicyclooctyl-5-carbonyl, N,N-dimethyl-2-[4-fluoro] phenyl-glycyl, N-methyl-[2,2,5,5-tetramethyl]-thiazolidine-2-carbonyl, 2-(R,S)-ethyl-2-phenylglycyl, D,L-2-aminoindane-1-carbonyl, N,N-dimethyl-2-(R, S)-methyl-2-phenylglycyl, 2-[N,N-dimethylamino] indane-2-carbonyl, 5-[N,N-dimethylamino]-5,6,7,8-tetrahydro-naphthalene-5-carbonyl, N-isopropyl-2-(R, S)-ethyl-2-phenylglycyl, 1-[N,N-dimethylamino] indane-2-carbonyl, N,N-dimethyl-2-propyl-2-phenylglycyl, N,N-dimethyl-2-[4-methoxy]phenyl-glycyl, N-methyl-3-hydroxy-D,L-valyl, N,N-dimethyl-D,L-2-isopropyl-2-phenylglycyl, N-methylpiperidine-2-carbonyl, N-methyl-L-prolyl, N-methyl-1,2,3,4-tetrahydroisoquinoline-1-carbonyl, N-methylazetidine-2-carbonyl, N-isopropylazetidine-2-carbonyl, N,N-dimethyl-[O-methyl]seryl, N,N-dimethyl-[O-methyl] threonyl, N-methyl-1,2,3,4-tetrahydroisoquinoline-3-carbonyl, 1-[N,N-dimethylamino]cyclohexyl-1-carbonyl, 1-[N,N-dimethylamino]cyclopentyl-1-carbonyl and 1,2,3,4-tetrahydroisoquinoline-3-carbonyl;
B is an amino acid residue selected from the group consisting of valyl, isoleucyl and 2-tert-butylglycyl;
D is an amino acid residue selected from the group consisting of N-methylvalyl, N-methylisoleucyl and N-methyl-L-2-t-butylglycyl;
E and F are each an amino acid residue independently selected from the group consisting of prolyl, thiaprolyl, homoprolyl, hydroxyprolyl, 3,4-didehydroprolyl, 4-fluoroprolyl, and 3-methylprolyl; and L is an alkoxy group or an amino group of the formula $R^1_l$—N—$R^2_l$, wherein $R^1_l$ and $R^2_l$ are independently selected from the group consisting of hydrogen, alkoxy, hydroxy, alkyl and alkylaryl.

37. A compound of the formula

A-B-D-E-F-L, wherein

A is an amino acid derivative selected from the group consisting of D-N-methyl-piperidine-2-carbonyl, N-ethyl-D-piperidine-2-carbonyl, N-isopropyl-D-piperidine-2-carbonyl, N,N-dimethyl-2-cyclopropyl-glycyl, N-methyl-D-prolyl, 1-aza-[3,3,0]bicyclooctyl-5-carbonyl, N-methyl-[2,2,5,5-tetramethyl]-thiazolidine-2-carbonyl, 2-(R,S)-ethyl-2-phenylglycyl, D,L-1-aminoindane-1-carbonyl, N,N-dimethyl-2-(R,S)-methyl-2-phenylglycyl, 5-[N,N-dimethylamino]-5,6,7,8-tetrahydro-naphthalene-5-carbonyl, 1-[N,N-dimethylamino]indane-2-carbonyl, N,N-dimethyl-2-propyl-2-phenylglycyl, N-methyl-3-hydroxy-D,L-valyl, N,N-dimethyl-D,L-2-isopropyl-2-phenylglycyl, N-methyl-piperidine-2-carbonyl, N-methyl-D,L-prolyl, N-methyl-1,2,3,4-tetrahydroisoquinoline-1-carbonyl, N-ethylazetidine-2-carbonyl, N-isopropylazetidine-2-carbonyl, N,N-dimethyl-[O-methyl]seryl, 1-[N,N-dimethylamino]cyclohexyl-1-carbonyl, N,N-dimethyl-D-2-ethyl-2-phenylglycyl, N,N-dimethyl-L-2-ethyl-2-phenylglycyl, and 1-[N,N-dimethylamino]cyclopentyl-1-carbonyl;

B is valyl;

D is N-methylvalyl;

E and F are each prolyl; and

L is a $C_1$–$C_6$-alkoxy group or an amino group of the formula $R^1_l$—N—$R^2_l$, wherein $R^1_l$ and $R^2_l$ are independently selected from the group consisting of hydrogen, $C_1$–$C_6$-alkoxy, hydroxy, normal, cyclic or branched $C_1$–$C_{10}$-alkyl, and phenylalkyl.

38. A method for treating cancer in a mammal, comprising administering to the mammal a therapeutically effective amount of a compound of claim 1.

39. The method of claim 38 wherein the mammal is a human.

* * * * *

UNITED STATES PATENT AND TRADEMARK OFFICE
CERTIFICATE OF CORRECTION

PATENT NO. : 6,143,721
DATED : November 7, 2000
INVENTOR(S) : Bernd Janssen, Teresa Barlozzari, Andreas Haupt, Thomas Zierke and Andreas Kling It is certified that error appears in the above-identified patent and that said Letters Patent is hereby corrected as shown below:

Column 30, Claim 1, in formula IIIa, delete "$R_a^2$" and insert -- "$R_a^{6''}$" --;
Column 31, Claim 1, line 15, after $R_a^1$ insert -- is -- ;
Column 31, Claim 1, line 51, delete "2-azabicyclo[2.2.1]heptane-3-carboxylic," and insert -- "2-azabicycloheptane-3-carboxylic" --;
Column 33, Claim 1, line 19, delete "n," and insert -- $n_e$ --;
Column 38, Claim 26, line 38, delete "-O-(CH2CH2O)$_d^1$-$_{CH3}$" and insert -- -O-(CH2CH2O)$_d^1$-CH$_3$ -- ;
Column 42, Claim 36, line 43, delete "D,L-2-aminoindane-1-carbonyl," and insert -- D,L-1-aminoindane-1-carbonyl --.

Signed and Sealed this

Eighth Day of May, 2001

*Attest:*

NICHOLAS P. GODICI

*Attesting Officer*  *Acting Director of the United States Patent and Trademark Office*